United States Patent
Wolton et al.

(10) Patent No.: US 9,844,363 B2
(45) Date of Patent: Dec. 19, 2017

(54) BIOPSY DEVICE WITH ASPIRATION VALVE

(71) Applicant: HOLOGIC, INC., Marlborough, MA (US)

(72) Inventors: Peter Wolton, Louisville, CO (US); Daniel Robertson, Denver, CO (US); Thomas Fisk, Newton, MA (US); Joseph A. Stand, III, Holden, MA (US); Christian M. Ulm, Newton, MA (US); Carl Pierce, Appleton, WI (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 15/024,631

(22) PCT Filed: Sep. 24, 2015

(86) PCT No.: PCT/US2015/052017
§ 371 (c)(1),
(2) Date: Mar. 24, 2016

(87) PCT Pub. No.: WO2016/049354
PCT Pub. Date: Mar. 31, 2016

(65) Prior Publication Data
US 2017/0000466 A1    Jan. 5, 2017

Related U.S. Application Data

(60) Provisional application No. 62/055,338, filed on Sep. 25, 2014.

(51) Int. Cl.
*A61B 10/02* (2006.01)
(52) U.S. Cl.
CPC ...... *A61B 10/0275* (2013.01); *A61B 10/0283* (2013.01); *A61B 2010/0208* (2013.01)

(58) Field of Classification Search
CPC .................. A61B 10/0275; A61B 2010/0208
See application file for complete search history.

(56) References Cited

U.S. PATENT DOCUMENTS

| 4,549,554 A | 10/1985 | Markham |
|---|---|---|
| 6,017,316 A | 1/2000 | Ritchart et al. |
| (Continued) | | |

FOREIGN PATENT DOCUMENTS

| GB | 2018601 | 10/1979 |
|---|---|---|
| WO | 81/01363 | 5/1981 |
| (Continued) | | |

OTHER PUBLICATIONS

PCT International Search Report and Written Opinion of the International Search Authority for PCT/US2015/052017, Applicant: Hologic Inc., Form PCT/ISA/210, 220, and 237, dated Feb. 15, 2016 (12 pages).

*Primary Examiner* — Rene Towa
(74) *Attorney, Agent, or Firm* — Vista IP Law Group LLP

(57) ABSTRACT

A biopsy device includes an instrument set and an instrument drive unit removably coupled to the instrument set. The instrument set includes an instrument set housing; an elongate outer cannula having a tissue receiving aperture in a side wall thereof; an elongate inner cannula disposed within an outer cannula lumen; an aspiration vent fluidly coupling the outer cannula lumen to atmosphere; and an aspirate valve in the aspiration vent, and configured such that the outer cannula lumen is vented to atmosphere only when the aspirate valve is open. The instrument drive unit includes a drive unit support structure removably coupled to the instrument set housing; a motorized inner cannula driver configured to axially oscillate the inner cannula relative to the outer cannula to sever tissue extending through the tissue receiving opening; and an actuating member configured to (Continued)

selectively mechanically prevent the aspirate valve from closing.

11 Claims, 21 Drawing Sheets

(56) References Cited

U.S. PATENT DOCUMENTS

| | | | |
|---|---|---|---|
| 6,032,673 A | 3/2000 | Savage et al. | |
| 6,432,083 B1 * | 8/2002 | Raschbaum | A61M 1/0001 604/118 |
| 7,662,109 B2 | 2/2006 | Hibner | |
| 7,867,173 B2 | 1/2011 | Hibner et al. | |
| 8,038,627 B2 | 10/2011 | Hibner | |
| 8,177,728 B2 | 5/2012 | Hibner et al. | |
| 8,235,913 B2 | 8/2012 | Hibner et al. | |
| 8,911,381 B2 | 12/2014 | Hibner et al. | |
| 8,956,306 B2 | 2/2015 | Hibner | |
| 2003/0233054 A1 * | 12/2003 | Stephens | A61B 10/0275 600/566 |
| 2005/0065453 A1 | 3/2005 | Shabaz et al. | |
| 2007/0106176 A1 | 5/2007 | Mark et al. | |
| 2007/0239067 A1 | 10/2007 | Hibner et al. | |
| 2009/0171242 A1 * | 7/2009 | Hibner | A61B 10/0275 600/566 |
| 2009/0171243 A1 | 7/2009 | Hibner | |
| 2010/0152611 A1 | 6/2010 | Parihar et al. | |
| 2010/0160826 A1 | 6/2010 | Parihar | |
| 2010/0317997 A1 | 12/2010 | Hibner | |
| 2013/0218047 A1 * | 8/2013 | Fiebig | A61B 10/0275 600/563 |
| 2014/0276209 A1 | 9/2014 | Hibner | |

FOREIGN PATENT DOCUMENTS

| | | |
|---|---|---|
| WO | 2007/021905 | 2/2007 |
| WO | 2012/074885 | 6/2012 |

* cited by examiner

| step no. | biopsy phase | vacuum | aspirate valve | liquid flow | check valve | venting |
|---|---|---|---|---|---|---|
| 102 | before firing; IC at distal most location against cutting board | off | open | none | open | off |
| 104 | optional saline and/or anesthesia delivery before cutting cycle | off | open | under pressure | closed | off |
| 106 | IC at distal most location against cutting board | on, but blocked by cutting board | open due to blocked vacuum | minimal to none due to blocked vacuum | open | off |
| 108 | IC moving proximally from distal most location | on | closed | under vacuum | open | off |
| 110 | IC at proximal most location | on | closed | under vacuum | open | off |
| 112 | first half of cutting cycle; IC moving distally from proximal most location | on | closed | under vacuum | open | off |
| 114 | middle of cutting cycle; IC at distal most location against cutting board; stops in axial direction and continues to rotate briefly | on, but blocked by cutting board | open due to blocked vacuum | minimal to none due to blocked vacuum | open | off |
| 116 | second half of cutting cycle; IC moving proximally to proximal most position | on | opened by actuation | minimal to none due to venting | open | on |
|  | repeat steps 112-116 until biopsy is completed |  |  |  |  |  |

*FIG. 31*

| | Cycle Component | Duration | Prerequisites (Trigger) | IC | Saline Valve | Air Valve |
|---|---|---|---|---|---|---|
| 1 | Pre-Cut Vacuum | About 0.5 seconds | Completion of Post-Aspirate Lavage | Retracted | Closed | Closed |
| 2 | Biopsy Cut | < About 2 seconds | Completion of Pre-Cut Vacuum (Optional & Core Index Complete Message) | Forward Rotation into Dwell | Closed | Closed |
| 3 | IC Retraction | < About 2 seconds | Completion of Dwell | Dwell and Reverse Rotation | Open (for 0.5s) | Closed |
| 4 | Pre-Aspirate Lavage | About 0.5 seconds | Completion of Biopsy Cut | Reverse Rotation | Open | Closed |
| 5 | Aspiration | Minimum of 2 seconds with valve fully open | Completion of Biopsy IC Retract | Retracted | Closed | Open |
| 6 | Post-Aspirate Lavage | About 0.5 seconds | Completion of Aspiration | Retracted | Open | Closed |

FIG. 34

BIOPSY DEVICE WITH ASPIRATION VALVE

RELATED APPLICATION DATA

The present application is a National Phase entry under 35 U.S.C §371 of International Patent Application No. PCT/US2015/052017, having an international filing date of Sep. 24, 2015, which claims the benefit of priority under 35 U.S.C. §119 to U.S. provisional patent application Ser. No. 62/055,338, filed Sep. 25, 2014, which is hereby incorporated by reference into the present application in its entirety.

FIELD

The present disclosure generally relates to the field of tissue sampling and harvesting. More specifically, the disclosure relates to biopsy needle sets and devices for use therewith.

BACKGROUND

In the practice of diagnostic medicine, it is often necessary or desirable to perform a biopsy, or to sample selected tissue from a living patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

Biopsies are routinely performed on tissue using a biopsy device including a needle set. One known needle set includes an outer cannula having a pointed tip and a tissue receiving opening defined near its distal end, and an inner cannula having an open distal end surrounded by an annular cutting blade. The inner cannula is slidably disposed within the outer cannula so that it can close the tissue receiving opening, thereby cutting tissue prolapsing into the lumen of the outer cannula through the tissue receiving opening. In vacuum-assisted biopsy devices, a vacuum is used to draw the tissue into the tissue receiving opening and to draw excised tissue through the inner cannula to a location proximal of the inner cannula. An irrigation system may also be connected to the outer cannula to provide liquid to facilitate the biopsy. Liquids such as saline may facilitate the biopsy process. The liquid may also provide therapy, such as analgesia provided by an analgesic.

Vacuum-assisted biopsy devices are available in handheld (for use with ultrasound) and stereotactic (for use with X-ray) versions. Stereotactic devices are mounted to a stereotactic unit that locates the lesion and positions the needle for insertion. In preparation for a prone biopsy using a stereotactic device, the patient lies face down on a table, and the breast protrudes from an opening in the table. The breast is then compressed and immobilized by two mammography plates. The mammography plates create images that are communicated in real-time to the stereotactic unit. The stereotactic unit then signals the biopsy device and positions the device for insertion into the lesion by the operator. In contrast, when using the handheld model, the breast is not immobilized. Rather the patient lies on her back and the doctor uses an ultrasound device to locate the lesion. The doctor must then simultaneously operate the handheld biopsy device and the ultrasound device.

During vacuum-assisted biopsies, as the excised tissue advances proximally along the lumen of the inner cannula, a vacuum can be created behind (i.e., distal of) the advancing tissue. At some point in these instances, the excised tissue can stop advancing along the length of the inner cannula because the vacuum behind the excised tissue equals the vacuum in front (i.e., proximal) of the excised tissue that is attempting to draw the excised tissue through the inner cannula.

An exemplary vacuum-assisted biopsy device is described in U.S. Pat. No. 6,638,235, filed on May 23, 2001, and assigned to the same assignee as the instant application, the contents of which are incorporated by reference as though fully set forth herein. In the biopsy device described therein, a leak path between the atmosphere and the outer cannula lumen allows the portion of the portion of the inner cannula lumen distal of the excised tissue to equalize in pressure with the atmosphere. This atmospheric equalization relieves the vacuum behind the excised tissue, and aids in drawing the tissue down the length of the inner cannula.

While the vacuum-assisted biopsy device described in U.S. Pat. No. 6,638,235 is an improvement over previous biopsy devices, having two separate connections to the outer cannula (for irrigation and atmospheric equalization) adds to the size of the biopsy device.

SUMMARY

In accordance with one embodiment, a biopsy device includes an instrument set and an instrument drive unit removably coupled to the instrument set. The instrument set includes an instrument set housing. The instrument set also includes an elongate outer cannula having an axial lumen, a proximal portion coupled to the instrument set housing, and a distal portion having a tissue receiving aperture in a side wall thereof in communication with the lumen. The instrument set further includes an elongate inner cannula disposed within the outer cannula lumen. Moreover, the instrument set includes an aspiration vent fluidly coupling the outer cannula lumen to atmosphere. In addition, the instrument set includes an aspirate valve interposed in the aspiration vent, and configured such that, when the aspirate valve is open, the outer cannula lumen is vented to atmosphere through the aspiration vent, and when the aspirate valve is closed, the outer cannula lumen is not vented to atmosphere through the aspiration vent. The instrument drive unit includes a drive unit support structure removably coupled to the instrument set housing. The instrument drive unit also includes a motorized inner cannula driver configured to axially oscillate the inner cannula relative to the outer cannula during operation of the biopsy system, such that an open distal end of the inner cannula moves back and forth across the tissue receiving aperture to sever tissue extending there through. The instrument drive unit further includes an actuating member configured to selectively mechanically prevent the aspirate valve from closing.

In one or more embodiments, the instrument set includes an interference member that may be selectively mechanically actuated to prevent the aspirate valve from closing, where the actuating member selectively mechanically actuates the interference member. The actuating member may include a cam that is rotatably coupled to the drive unit support structure, where the cam may be rotated to mechanically actuate the interference member. The instrument drive unit also may include a motorized cam driver having an output operatively coupled to the cam for providing automatic rotation of the cam between a first position, in which the cam does not actuate the interference member, and a second position, in which the cam actuates the interference member. The motorized cam driver may be processor controlled to selectively rotate the cam into and out of the first position depending upon a respective position and a direction of travel of the inner cannula relative to the outer cannula.

In one or more embodiments, when the aspirate valve is open, the outer cannula lumen is vented to a non-sealed interior of the instrument set housing through the aspiration vent. The aspirate valve may be configured such that the aspirate valve remains closed unless the interference member is mechanically actuated to prevent the aspirate valve from closing. Alternatively, the aspirate valve may be configured such that the aspirate valve remains open unless the vacuum is supplied through the outer cannula. The aspirate valve may include a sealing member configured to seal a valve opening when a vacuum is supplied through the outer cannula.

In one or more embodiments, the drive unit support structure is configured for mounting to a stereotactic table adapter. The sealing member may include a ball, and the valve chamber opening may be located in a lateral sidewall of the valve chamber such that, when the drive unit support structure is mounted to the adapter and the instrument set housing is coupled to the instrument drive unit, the ball falls off the valve chamber opening under gravitational force in the absence of a vacuum source drawing the ball against the valve chamber opening. The outer cannula may be movable relative to the instrument set housing.

In one or more embodiments, the biopsy device also includes an actuating member configured to mechanically actuate the interference member. The actuating member may include a rotatable cam. The rotatable cam may be operatively coupled to a motorized cam driver. The motorized cam driver may be processor controlled to selectively rotate the cam into and out of a position that actuates the interference member depending upon a respective position and a direction of travel of the inner cannula relative to the outer cannula.

In accordance with another embodiment, a biopsy device includes an elongate outer cannula having a lumen and a tissue receiving aperture in a side wall thereof in communication with the lumen. The biopsy device also includes an elongate inner cannula disposed within the outer cannula lumen, the inner cannula removably coupled to a motorized cannula driver configured to axially oscillate the inner cannula relative to the outer cannula during operation of the biopsy device such that an open distal end of the inner cannula moves back and forth across the tissue receiving aperture to sever tissue extending there through. The biopsy device further includes an aspiration vent fluidly coupling the outer cannula lumen to atmosphere. Moreover, the biopsy device includes an aspirate valve interposed in the aspiration vent such that, when the aspirate valve is open, the outer cannula lumen is vented to atmosphere through the aspiration vent, and when the aspirate valve is closed, the outer cannula lumen cannot vent to atmosphere through the aspiration vent, the aspirate valve including a sealing member disposed in a valve chamber. In addition, the biopsy device includes an interference member. The respective sealing member and valve chamber are together configured such that the aspirate valve remains closed unless the interference member is selectively mechanically actuated to interfere with, and thereby prevent, the sealing member from sealing the valve chamber opening.

In one or more embodiments, the device has a housing and/or other support structure configured for mounting to a stereotactic table adapter. The sealing member may include a ball, and the valve chamber opening may be located in a lateral sidewall of the valve chamber such that, when the housing or other support structure is mounted to the adapter, the ball falls off the valve chamber opening under gravitational force in the absence of a vacuum source drawing the ball against the valve chamber opening. The device may also include a vacuum source fluidly coupled to a lumen of the inner cannula such that the vacuum source is also in fluid communication with the outer cannula lumen when an open distal end of the inner cannula is in fluid communication with the outer cannula lumen.

In accordance with still another embodiment, a biopsy apparatus includes an instrument set configured for removable coupling with an instrument drive unit, the instrument set including an instrument set housing; an elongate outer cannula having an axial lumen, a proximal portion coupled to the instrument set housing, and a distal portion having a tissue receiving aperture in a side wall thereof in communication with the lumen; an elongate inner cannula disposed within the outer cannula lumen; an aspiration vent fluidly coupling the outer cannula lumen to atmosphere; and an aspirate valve interposed in the aspiration vent, the inner cannula having a lumen in fluid communication with the tissue receiving aperture in the outer cannula via a distal opening in the inner cannula. A method of operating the biopsy apparatus includes introducing the distal portion of the biopsy apparatus in tissue so that the tissue receiving aperture in the outer cannula is positioned adjacent the tissue targeted for biopsy. The method also includes applying vacuum though a proximal end of the inner cannula lumen. The method further includes translating the inner cannula relative to the outer cannula to sever tissue prolapsed into the tissue receiving opening. Moreover, the method includes translating the inner cannula proximally relative to the outer cannula. In addition, the method includes opening the aspirate valve to draw air into the biopsy apparatus through the aspiration vent to relieve a vacuum formed distal of the severed tissue.

In one or more embodiments, the aspiration vent is fluidly coupled to a non-sealed interior of the instrument set housing. When the aspirate valve is open, the outer cannula lumen may vent to the non-sealed interior of the instrument set housing through the aspiration vent. The instrument set may include an interference member. The method may include selectively mechanically actuating the interference member to prevent the aspirate valve from closing.

In one or more embodiments, the method also includes removably coupling the instrument drive unit to the instrument set, where the instrument drive unit selectively mechanically opens the aspirate valve. The aspirate valve may be configured such that the aspirate valve remains open unless the vacuum is supplied through the outer cannula. The outer cannula may be movable relative to the instrument set housing.

In one or more embodiments, the instrument drive unit is removably coupled to the instrument set, and the instrument drive unit may include an actuating member. The method may include the actuating member selectively mechanically actuating the interference member. The actuating member may include a cam that is rotatably coupled to a drive unit support structure, and the method may also include rotating the cam to selectively mechanically actuate the interference member. The instrument drive unit may include a motorized cam driver having an output operatively coupled to the cam for providing automatic rotation of the cam between a first position, in which the cam does not actuate the interference member, and a second position, in which the cam actuates the interference member. The motorized cam driver may be processor controlled to selectively rotate the cam into and out of the first position depending upon a respective position and a direction of travel of the inner cannula relative to the outer cannula.

In one or more embodiments, the aspirate valve is configured such that the aspirate valve remains closed unless the interference member is mechanically actuated to prevent the aspirate valve from closing. The aspirate valve may include a sealing member configured to seal a valve opening when a vacuum is supplied through the outer cannula, and a valve chamber, where the sealing member is disposed in the valve chamber. The drive unit support structure may be configured for mounting to a stereotactic table adapter. The sealing member may include a ball, and the valve chamber opening being located in a lateral sidewall of the valve chamber such that, when the drive unit support structure is mounted to the adapter and the instrument set housing is coupled to the instrument drive unit. The method may include, when the vacuum is applied though the proximal end of the inner cannula lumen, the vacuum drawing the ball against the valve chamber opening.

In accordance with yet another embodiment, a biopsy device includes an elongate outer cannula having a lumen and a tissue receiving aperture in a side wall thereof in communication with the lumen. The biopsy device also includes an elongate inner cannula disposed within the outer cannula lumen, the inner cannula coupled to a motorized cannula driver configured to axially oscillate the inner cannula relative to the outer cannula during operation of the biopsy device such that an open distal end of the inner cannula moves back and forth across the tissue receiving aperture to sever tissue extending there through. The biopsy device further includes an aspiration vent fluidly coupling the outer cannula lumen to atmosphere. Moreover, the biopsy device includes an aspirate valve interposed in the aspiration vent such that, when the aspirate valve is open, the outer cannula lumen is vented to atmosphere through the aspiration vent, and when the aspirate valve is closed, the outer cannula lumen cannot vent to atmosphere through the aspiration vent, the aspirate valve including a sealing member disposed in a valve chamber. The respective sealing member and valve chamber are together configured such that the aspirate valve remains open unless the sealing member is drawn to seal a valve chamber opening by a vacuum supplied through the outer cannula lumen. In addition, the biopsy device includes an interference member that may be selectively mechanically actuated to interfere with, and thereby prevent, the sealing member from sealing the valve chamber opening.

It will be appreciated that the aspiration leak path of the biopsy device, including the inner and outer cannulas, aspiration vent, aspirate valve and interference member, may all be located in a disposable biopsy instrument set, with the respective valve actuating member located in a reusable drive unit along with the inner cannula driver.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

In FIG. 2, the cutting board is omitted for clarity.

In FIGS. 10 and 11 (detailed bottom views), the biopsy devices are in the same orientation as shown in FIG. 9 (bottom view).

In FIG. 12, the view is from above and to the left of the biopsy device with the distal end pointed to the left of the figure, as in FIG. 1.

In FIG. 13, the view is from above and to the left of the biopsy device with the distal end pointed to the left of the figure, as in FIG. 1.

In FIG. 15, portions of the aspiration and irrigation system are shown in phantom for clarity. In FIG. 15, the view is from above and to the left of the biopsy device with the distal end pointed to the left of the figure, as in FIG. 1.

In FIG. 16, the biopsy device has been rotated onto its left side and the view is from the top of the device (on the left side of the figure) with the distal end pointed to the left of the figure. In FIG. 17, the view is from above and to the left of the biopsy device with the distal end pointed to the left of the figure, as in FIG. 1.

In FIG. 18, the view is from above and to the left of the biopsy device with the distal end pointed to the left of the figure, as in FIG. 1.

In FIG. 21, the distal end of the biopsy device is pointed to the right of the figure.

In FIG. 22, other components are shown in phantom for clarity.

FIGS. 25 to 28 axially progress through the aspiration and irrigation system from proximal of the cam follower to the distal of the cam follower.

FIG. 31 is a table summarizing a biopsy procedure and that states of the check and aspirate valves and various irrigation and aspiration/venting related functions at the respective steps in the procedure, according to one embodiment.

FIG. 34 is a table summarizing the steps of the vacuum-assisted biopsy procedure illustrated in FIG. 33.

DETAILED DESCRIPTION OF THE ILLUSTRATED EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. As used in this specification, "reusable" devices and portions thereof include, but are not limited to, devices that are configured and intended to be used in multiple procedures. As used in this specification, "disposable" devices and portions thereof include, but are not limited to, devices that are configured and intended to be used in only one procedure. After being used in a procedure, disposable devices are configured and intended to be discarded. One difference between reusable and disposable medical devices is that contamination is a concern with the former but not the latter because disposable medical devices are not reused.

Various embodiments of the disclosed inventions are described hereinafter with reference to the figures. It should be noted that the figures are not drawn to scale. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

Figure 1:
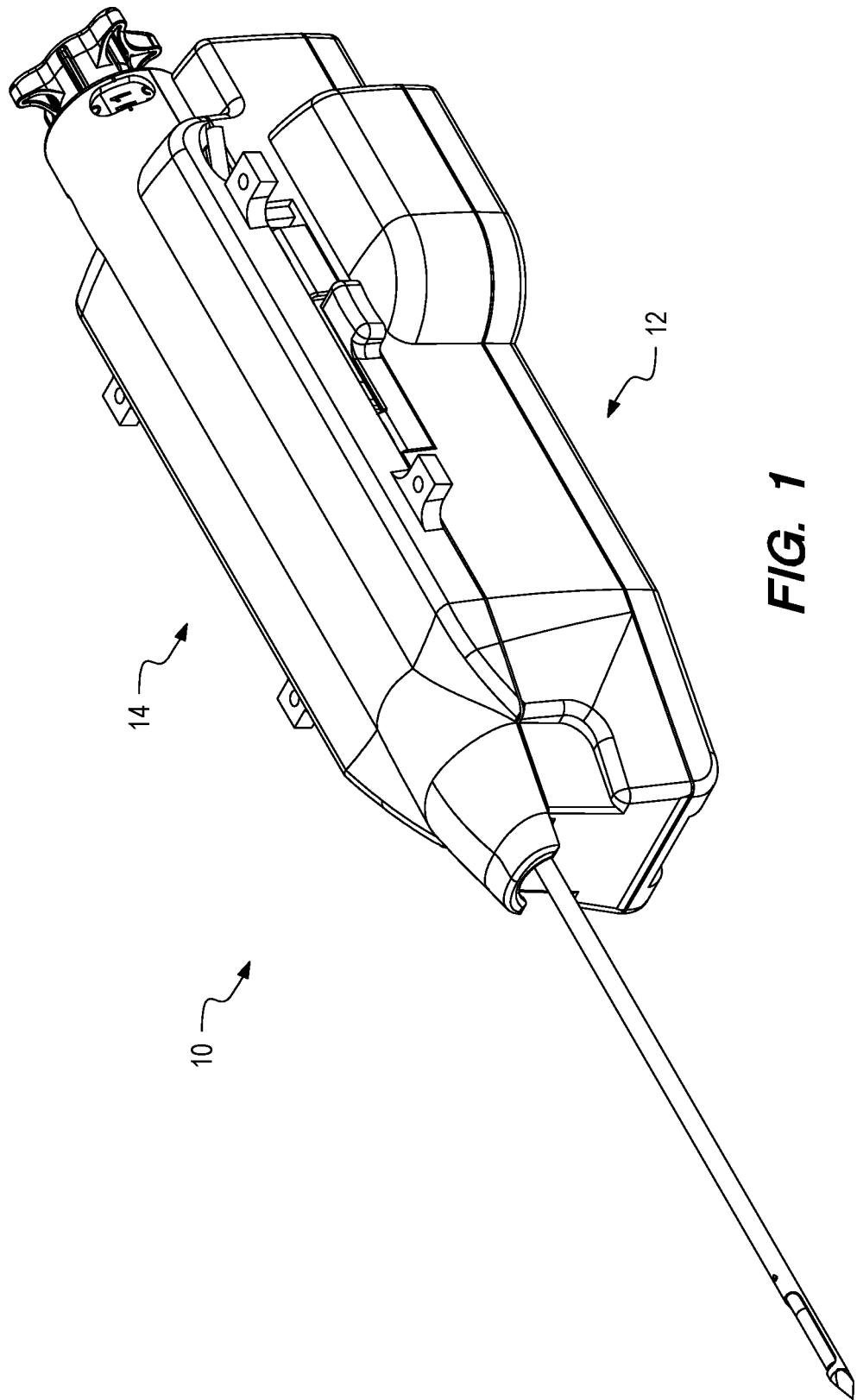
FIG. 1 is a perspective view of a biopsy device according to one embodiment.

FIG. 1 depicts a biopsy device 10 in accordance with one embodiment. The biopsy device 10 includes a reusable body portion 12 and a disposable needle portion 14. The reusable body portion 12 includes components configured to perform a tissue biopsy using the disposable needle portion 14. These components include a drive assembly configured to drive movement of components of the disposable needle portion 14. An exemplary drive system is described in U.S. Provisional Patent Application Ser. No. 62/055,610, filed Sep. 25, 2014, and assigned to the same assignee as the instant application, the contents of which are incorporated by reference as though fully set forth herein. The drive assembly can include one or more motors known in the art, including electrical, pneumatic or hydraulic motors. The reusable body portion 12 also includes a controller (e.g., a computer processor) configured to control the motors in the drive assembly and thereby control movement of the components of the disposable needle portion 14.

Further, the reusable body portion 12 includes an elongate cam configured to lock and unlock various components of the reusable body portion 12 in various modes of the biopsy procedure as described in the above-incorporated patent application. In alternative embodiments, the elongate cam can have either: (1) grooves and slots for interacting with detents or pegs; or (2) lobes or cams for interacting with strike-plates. The interactions in both of these embodiments facilitate locking and unlocking described above. These embodiments are described in U.S. Provisional Patent Application Ser. No. 62/055,610 (incorporated by reference above) and U.S. Utility patent application Ser. No. 14/864,432, filed concurrently herewith, and assigned to the same assignee as the instant application, the contents of which are incorporated by reference as though fully set forth herein. Elongate cams can include any elongated member comprising features configured to control movement of other device components, For instance, in other embodiments, the elongate cam can have both: (1) grooves and slots; and (2) lobes or cams.

Figure 2:
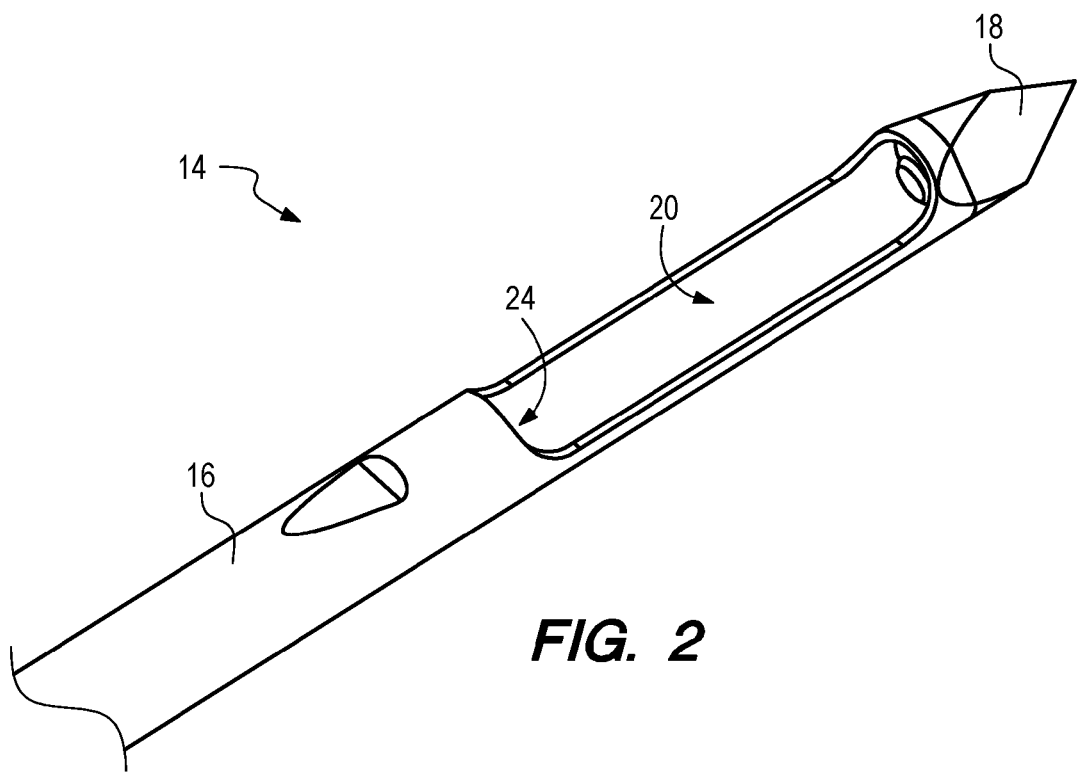
FIGS. 2 and 4 are perspective views of the outer cannula of the biopsy device depicted in FIG. 1.
Figure 3:
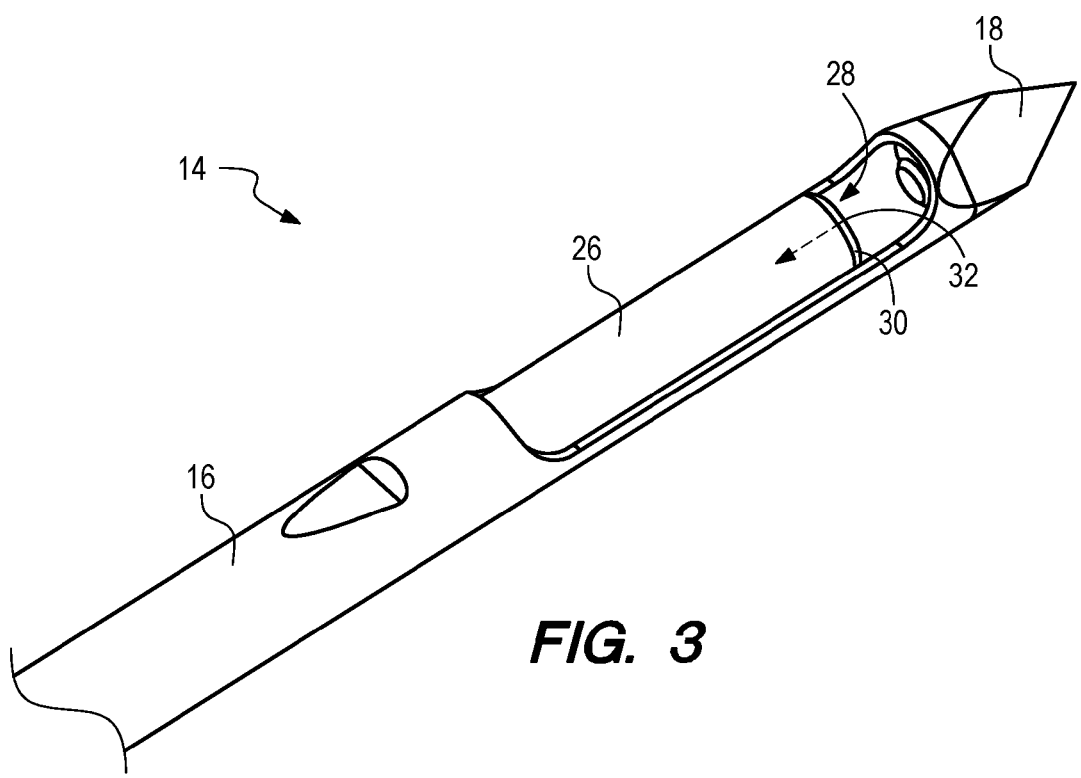
FIG. 3 is a perspective view of the inner and outer cannulas of the biopsy device depicted in FIG. 1. The cutting board is omitted for clarity.

FIGS. 2 and 3 depict respective distal portions of the disposable needle portion 14. FIG. 2 shows the outer cannula 16 without the inner cannula 26. FIG. 3 shows the outer cannula 16 with a distal portion of the inner cannula 26 visible through a tissue receiving opening 20. The disposable needle portion 14 includes an outer cannula 16 having a distal tissue piercing tip 18. The outer cannula defines an outer cannula lumen 24 and the tissue receiving opening 20 adjacent to the distal tissue piercing tip 18, the tissue receiving opening 20 being in fluid communication with the outer cannula lumen 24. A biopsy device 10 having a variable size tissue receiving opening 20 is described in U.S. patent application Ser. No. 14/497,046, filed Sep. 25, 2014, and assigned to the same assignee as the instant application, the contents of which are incorporated by reference as though fully set forth herein. In the disposable needle portion 14, the inner cannula 26 is slidably disposed in the outer cannula lumen 24 and has an open distal end 28 surrounded by an annular cutting blade 30 (FIG. 3). When the inner cannula 26 is in its distal-most position in the outer cannula lumen 24, the inner cannula 26 closes the tissue receiving opening 20 in the outer cannula 16.

Figure 4:
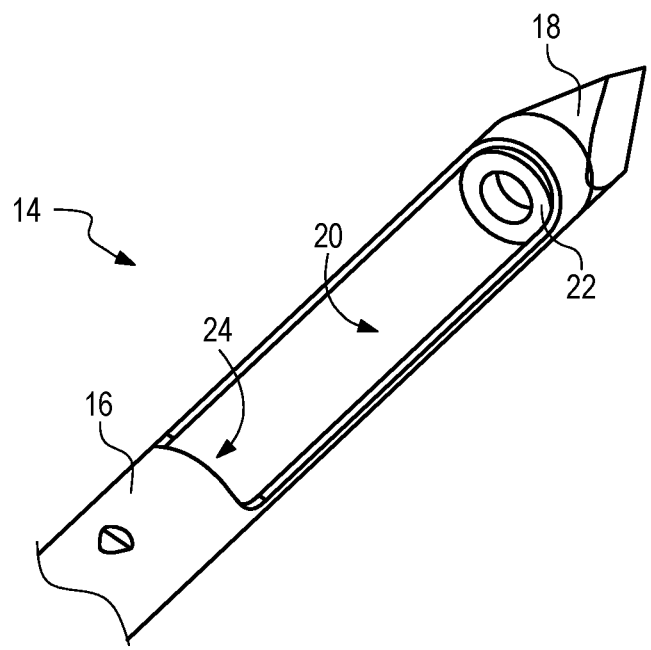
Figure 5:
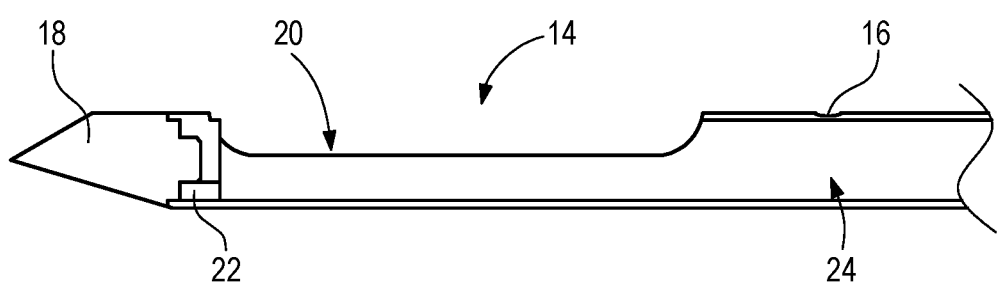
FIG. 5 is a longitudinal cross-sectional view of the outer cannula of the biopsy device depicted in FIG. 1.

As shown in FIGS. 4 and 5, a cutting board 22 is disposed in the outer cannula lumen 24 distal to the tissue receiving opening 20. The cutting board 22 is configured to seal the open distal end 28 of the inner cannula 26 when the inner cannula 26 is in contact with the cutting board 22. This seal prevents fluids introduced into the outer cannula lumen 24 from being aspirated through the open distal end 28 and the inner cannula lumen 32, and bypassing the biopsy site. Instead, the fluids are delivered to the tissue through the outer cannula lumen 24 and the tissue receiving opening 20.

Figure 6:
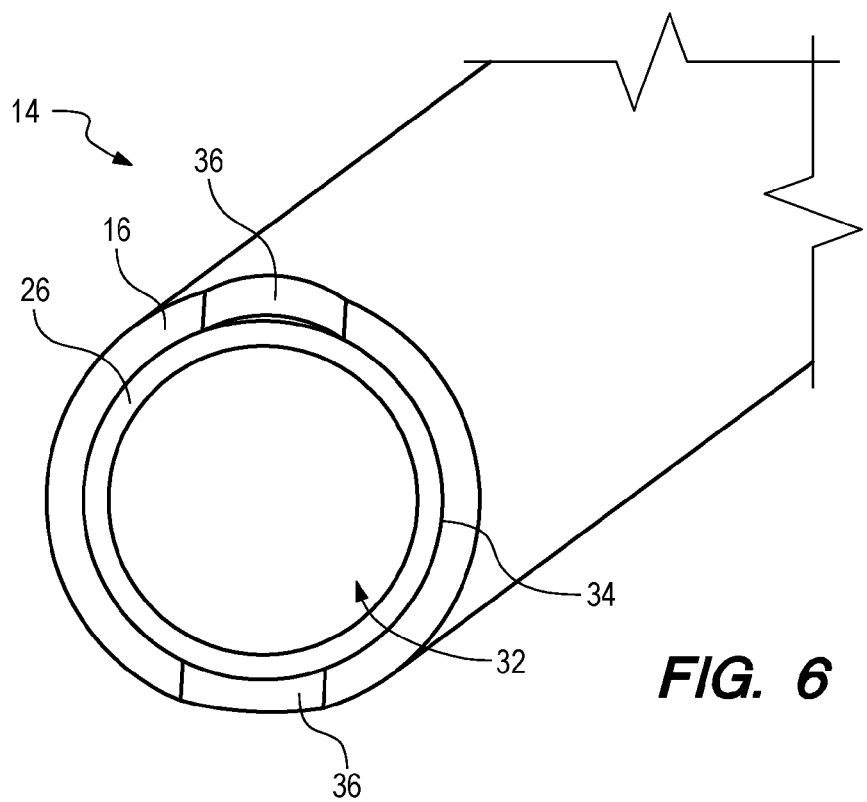
FIGS. 6 and 7 are axial cutaway views through the inner and outer cannulas the biopsy device depicted in FIG. 1 at the level of the side openings in the outer cannula.
Figure 7:
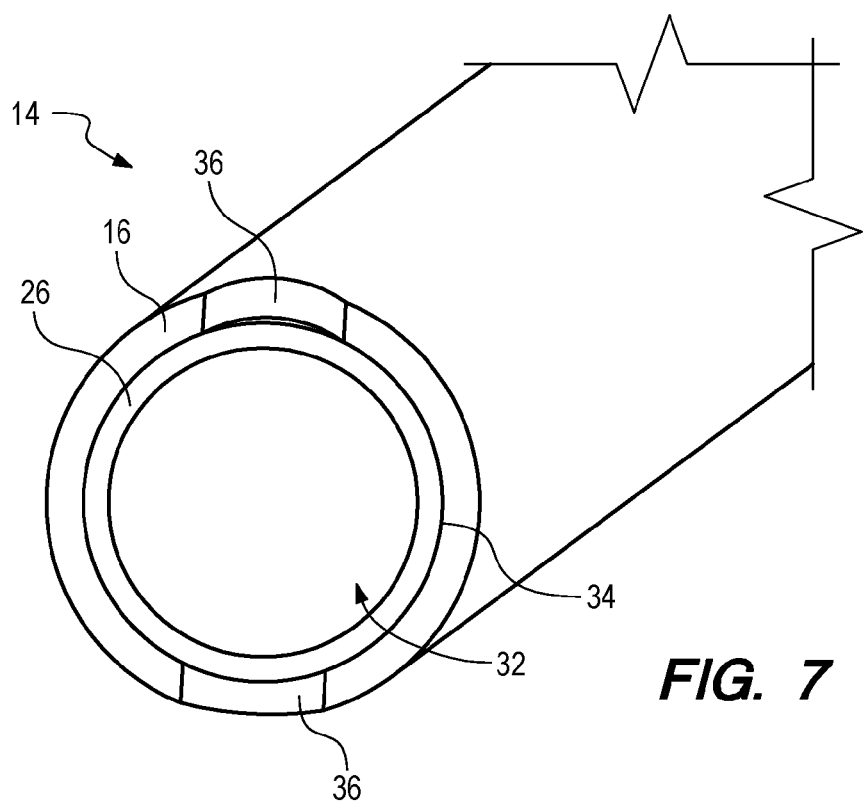

FIGS. 6 and 7 are axial cross-sectional views through respective portions of the outer and inner cannulas 16, 26 with other components of the disposable needle portion 14 omitted for clarity. As shown in FIGS. 6 and 7, the outer and inner cannulas 16, 26 form an annular lumen 34 there between. The annular lumen 34 is the portion of the outer cannula lumen 24 that is not occupied by the inner cannula 26. The outer cannula 16 also defines two side openings 36 in communication with the annular lumen 34.

Figure 8:
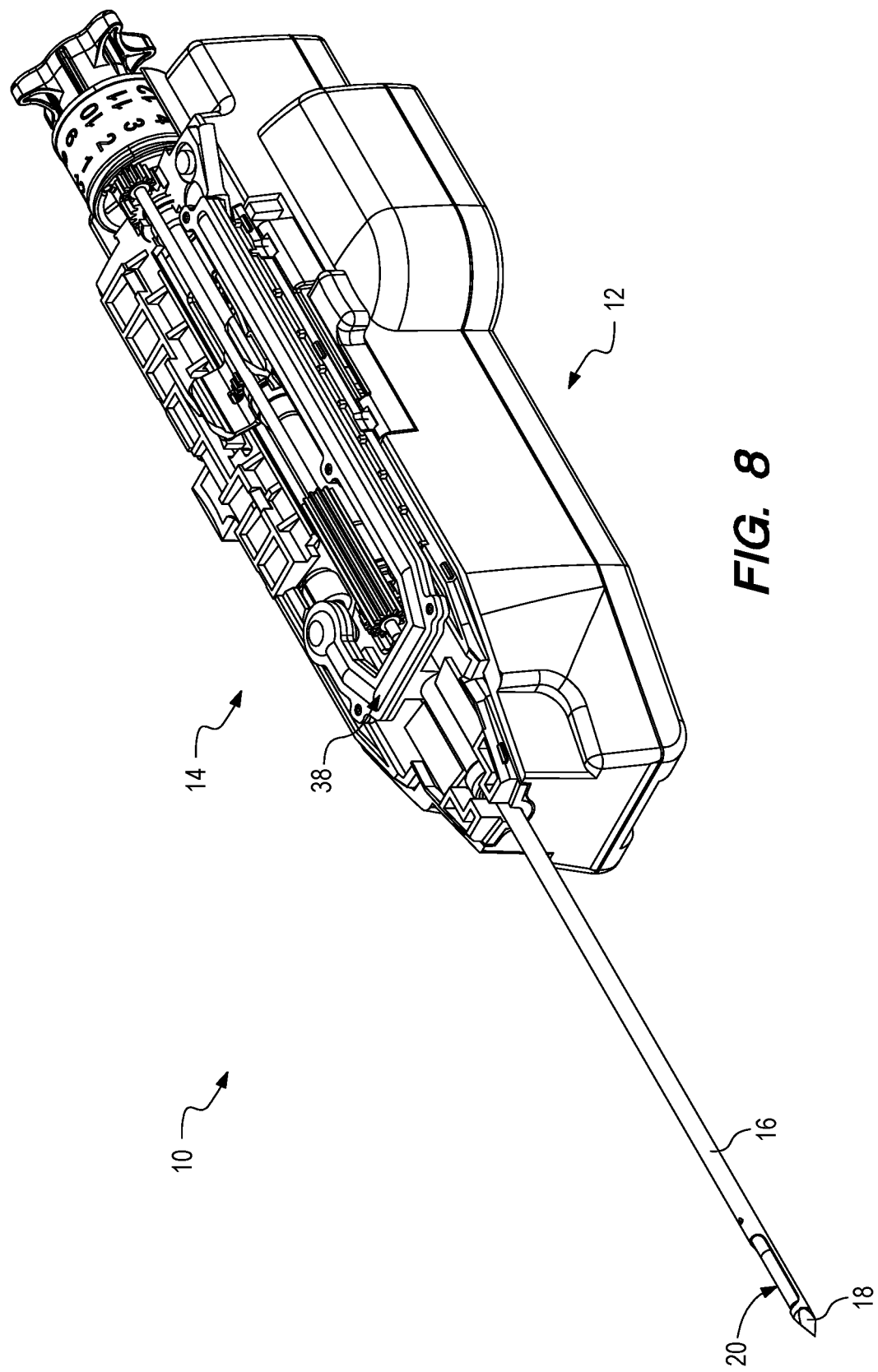
FIG. 8 is a perspective view of the biopsy device depicted in FIG. 1 with the top housing of the disposable needle portion omitted for clarity.
Figure 9:
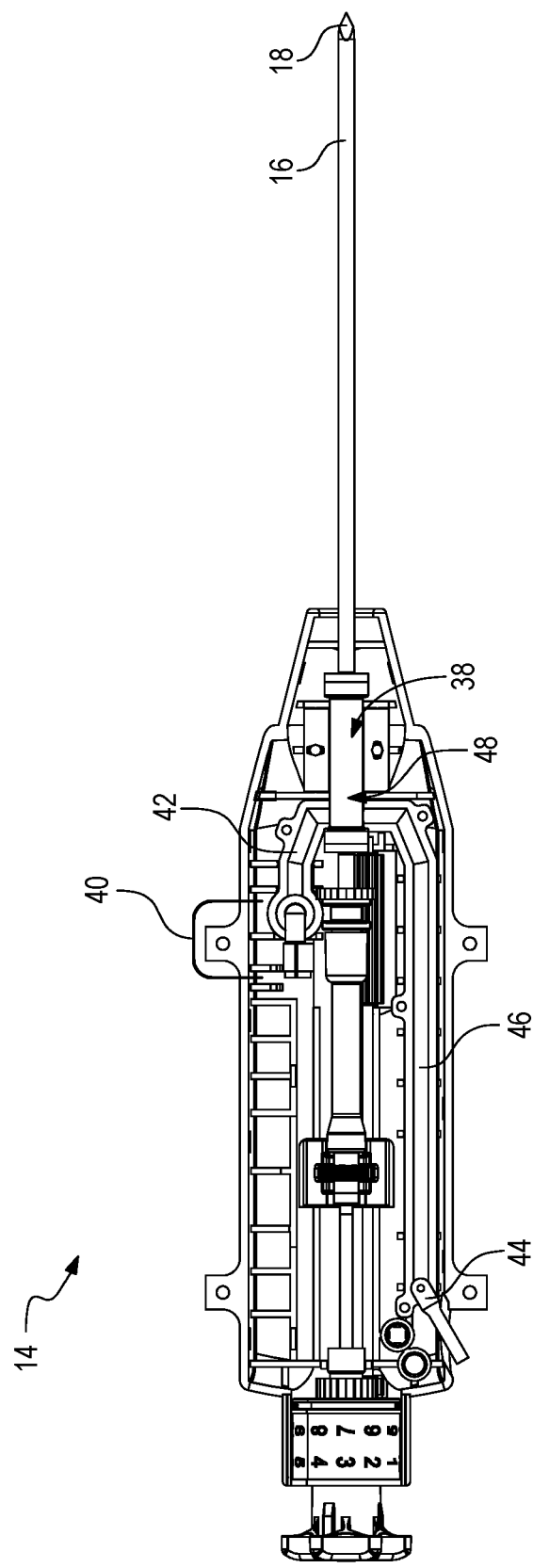
FIGS. 9 to 11 are wide (FIG. 9) and detailed (FIGS. 10 and 11) bottom views of the disposable needle portion of the biopsy device depicted in FIG. 1 with the bottom housing and adjacent components omitted for clarity.

FIG. 8 depicts the biopsy device 10 with the top housing of the disposable needle portion 14 omitted to facilitate visualization of the aspiration and irrigation system 38 relative to other components of the disposable needle portion 14. FIG. 9 depicts the disposable needle portion 14 of a biopsy device 10 from a bottom view to facilitate visualization of the aspiration and irrigation system 38 therein.

Figure 10:
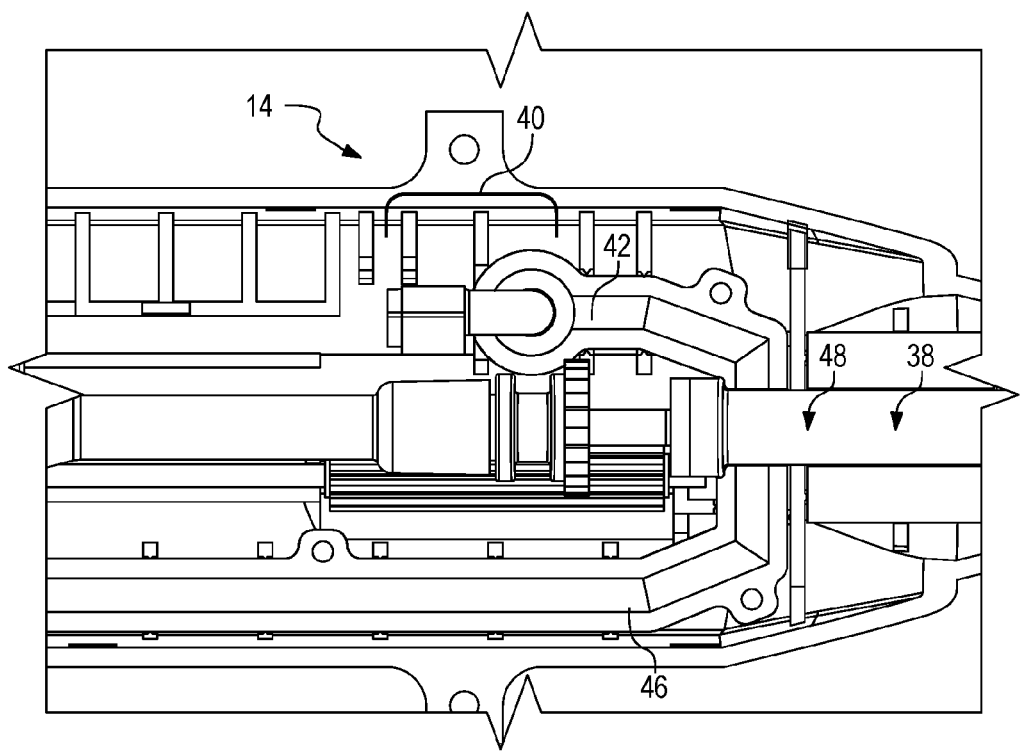
Figure 11:
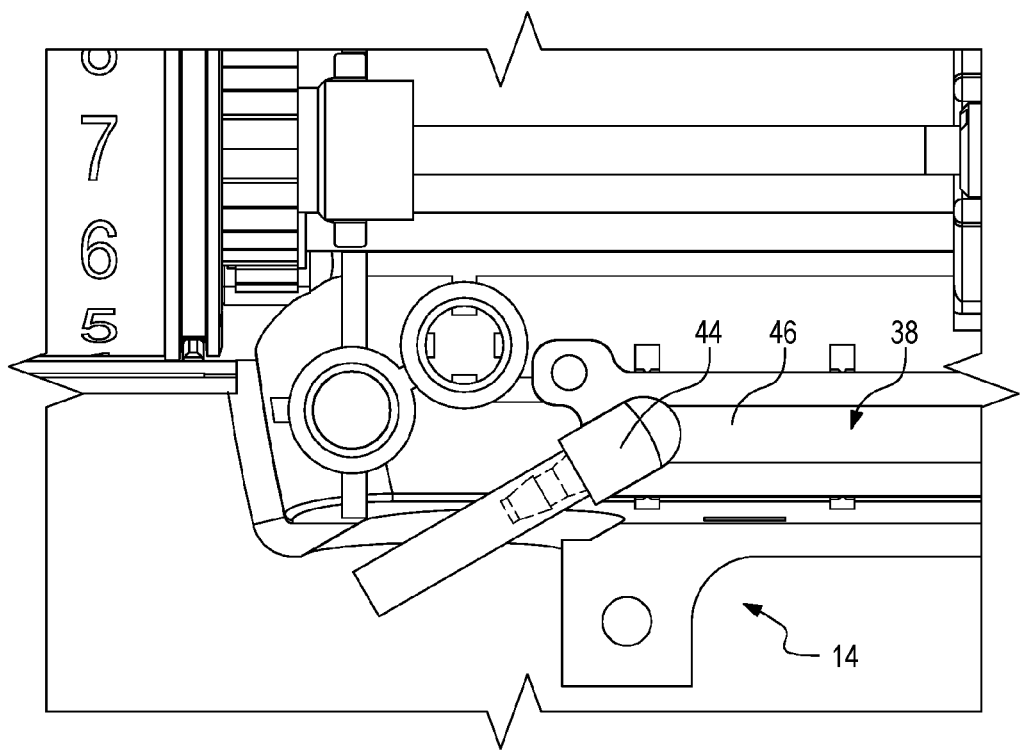
Figure 12:
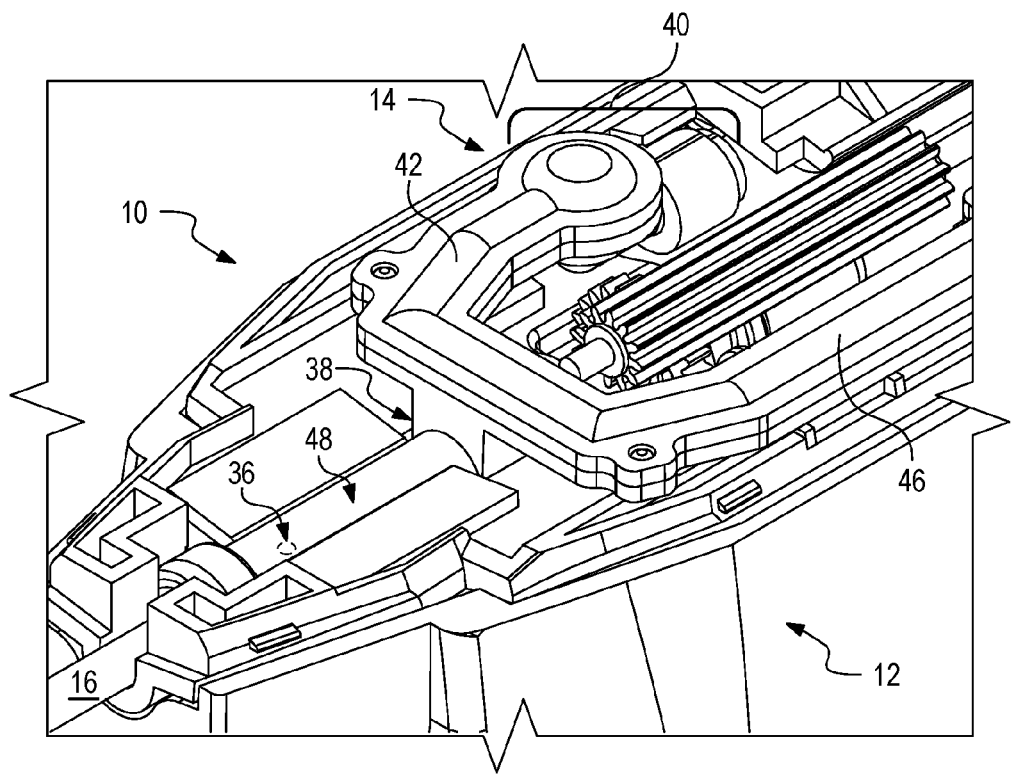
FIG. 12 is a detailed perspective view of the biopsy device depicted in FIG. 1 with the top housing and adjacent components of the disposable needle portion omitted and portions of the aspiration and irrigation system shown in phantom for clarity.
Figure 13:
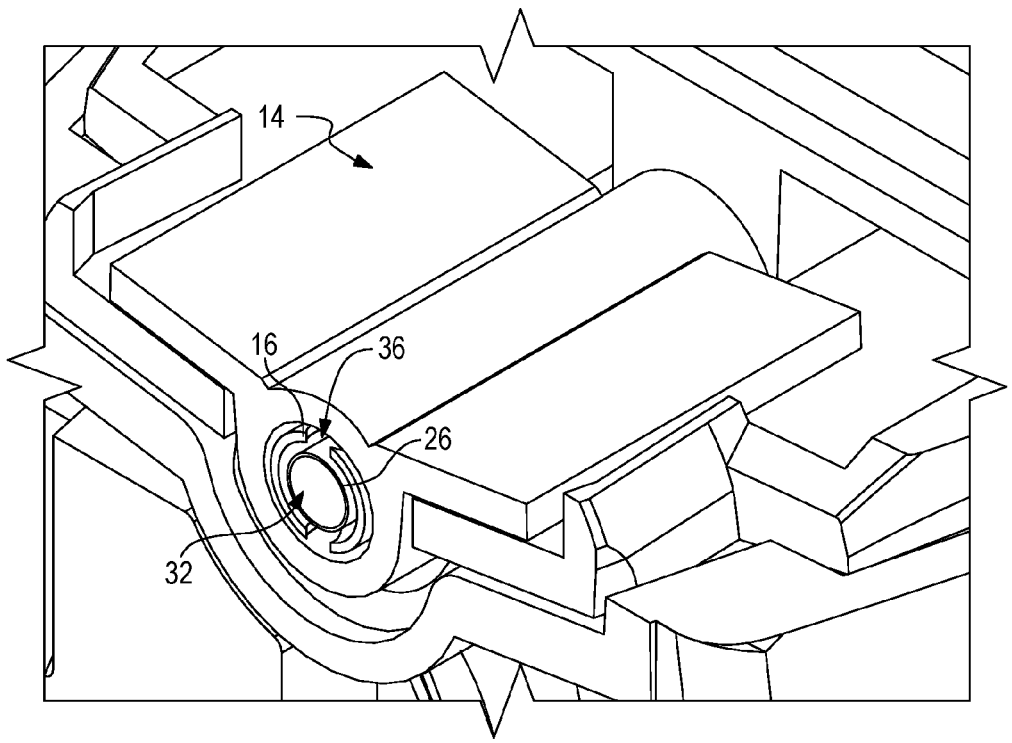
FIG. 13 is an axial cutaway perspective view through the biopsy device depicted in FIG. 1 with the top housing and adjacent components of the disposable needle portion omitted and portions of the aspiration and irrigation system shown in phantom for clarity. The axial cutaway is at the level of the side openings in the outer cannula.

As shown in FIGS. 10 and 11, the aspiration and irrigation system 38 includes an aspiration vent 40 fluidly coupled to an aspiration line 42 and an irrigation input 44 fluidly coupled to an irrigation line 46. The aspiration line 42 and irrigation line 46 are each in turn fluidly coupled to a manifold 48. As shown in FIGS. 12 and 13, the manifold 48 is in turn fluidly coupled to the side openings 36 in the outer cannula 16, which lead to the annular lumen 34 therein.

Figure 14:
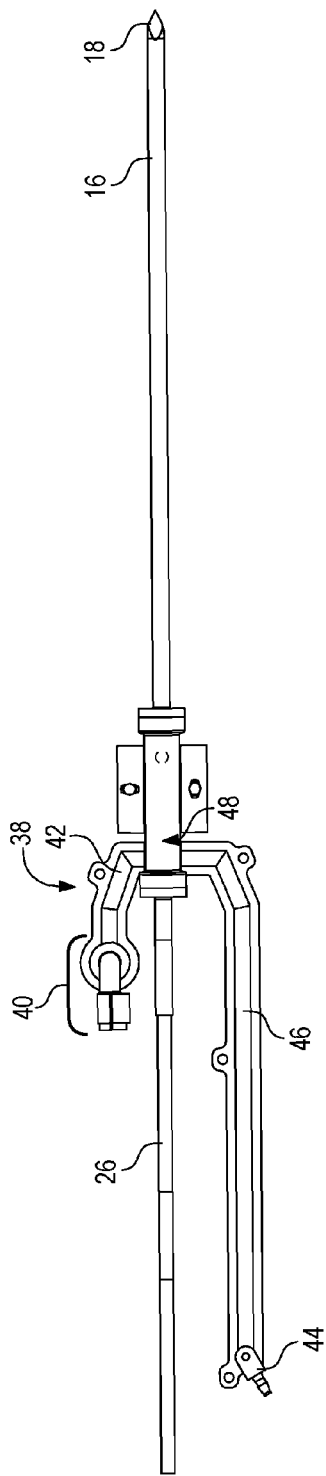
FIGS. 14 and 15 are bottom and perspective views of the inner and outer cannulas and the aspiration and irrigation system of the biopsy device depicted in FIG. 1.
Figure 15:
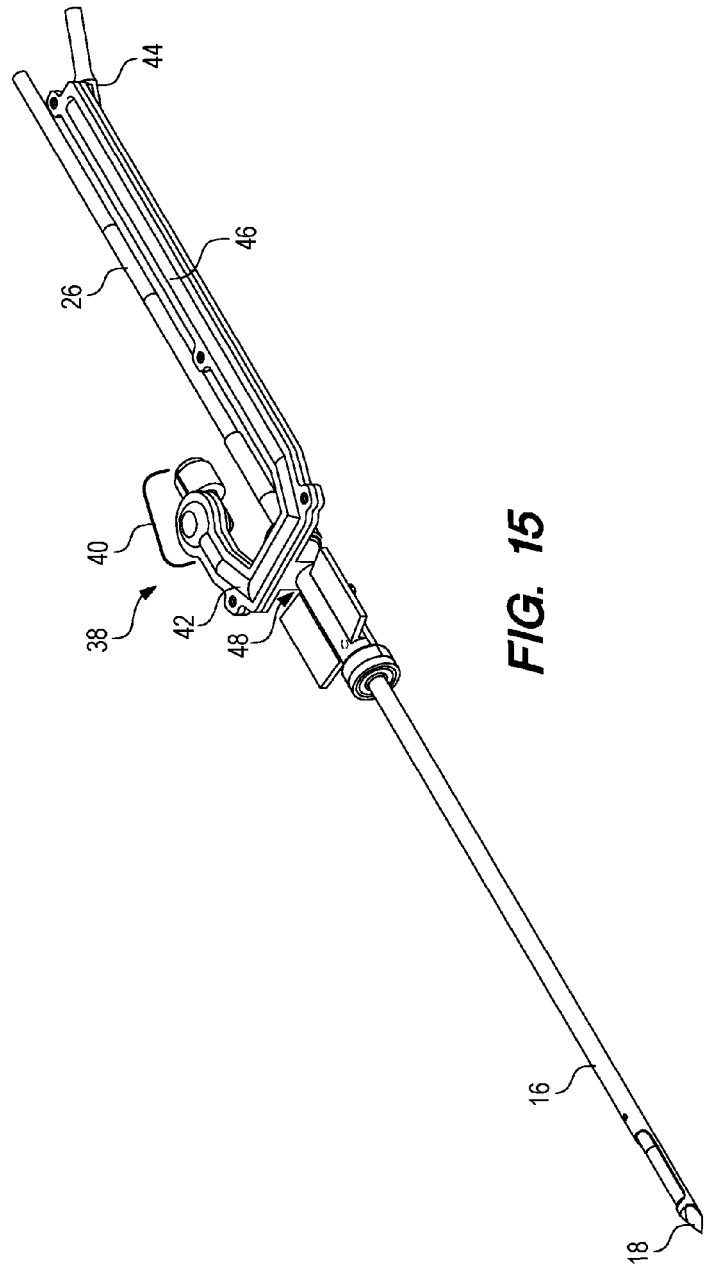
Figure 29:
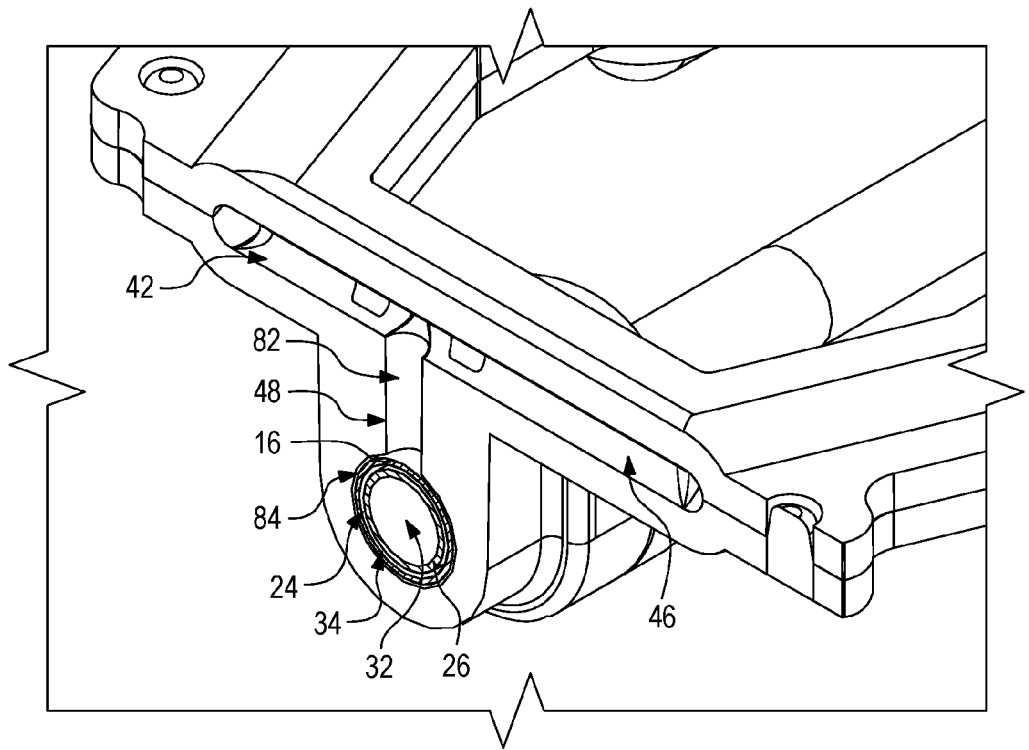
FIGS. 29 and 30 are axial and longitudinal cutaway views through the inner and outer cannulas and the aspiration and irrigation system of the biopsy device depicted in FIG. 1, with portions shown in phantom for clarity. The axial cutaway view is at the level where the aspiration and irrigation lines join the manifold. The longitudinal cutaway view is at the level of the outer and inner cannula lumens.
Figure 30:
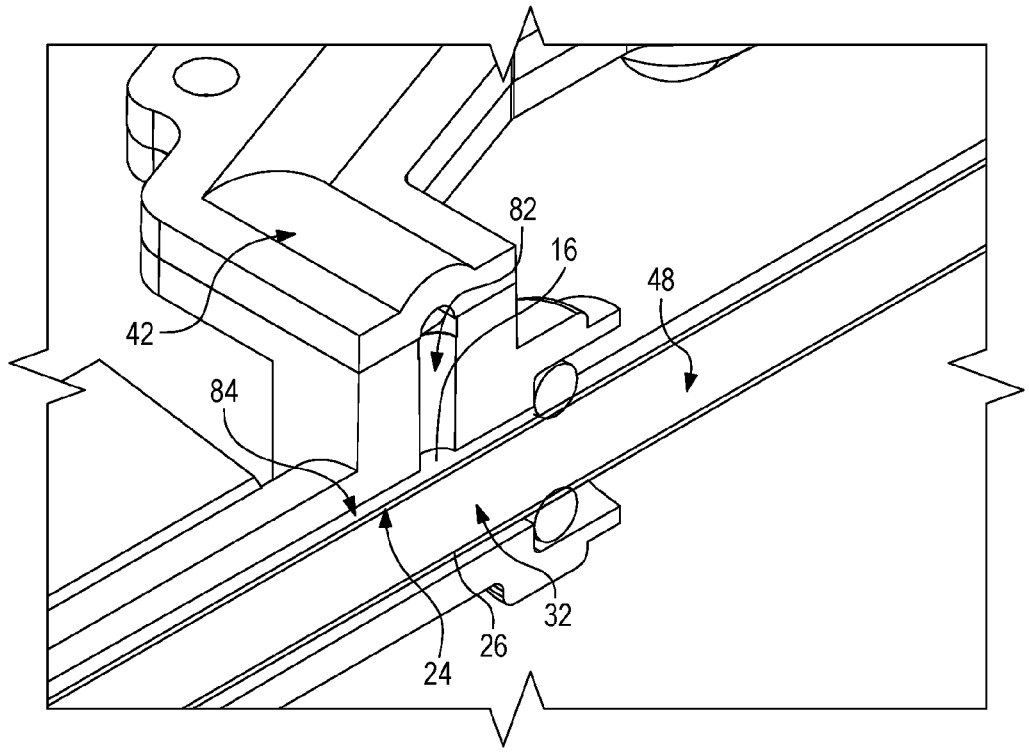

FIGS. 14 to 18, 29 and 30 depict the aspiration and irrigation system 38 and the outer and inner cannulas 16, 26 with all other components of the disposable needle portion 14 of the biopsy device 10 omitted for clarity. FIGS. 14 and 15 depict the aspiration and irrigation system 38 and the outer and inner cannulas 16, 26 in respective bottom and perspective wide views. In FIG. 15, the aspiration and irrigation system 38 is shown in phantom for clarity. FIG. 29 is an axial cutaway view of the aspiration and irrigation system 38 and the outer and inner cannulas 16, 26 at the level where the aspiration and irrigation lines 42, 46 join the manifold 48. FIG. 30 is a longitudinal cutaway view of the aspiration and irrigation system 38 and the outer and inner cannulas 16, 26 at the level of the outer and inner cannula lumens 24, 32. As shown in FIGS. 29 and 30, the manifold 48 is a space including a cylindrical portion 82 in fluid communication with the lumens of the aspiration and irrigation lines 42, 46 at a "T" junction. The manifold 48 also includes an annular portion 84 in fluid communication with the cylindrical portion 82, and therefore with the lumens of the aspiration and irrigation lines 42, 46. The annular portion 84 is disposed around and approximately coaxial with portions of the outer and inner cannulas 16, 26 and the annular lumen 34 therebetween.

Figure 16:
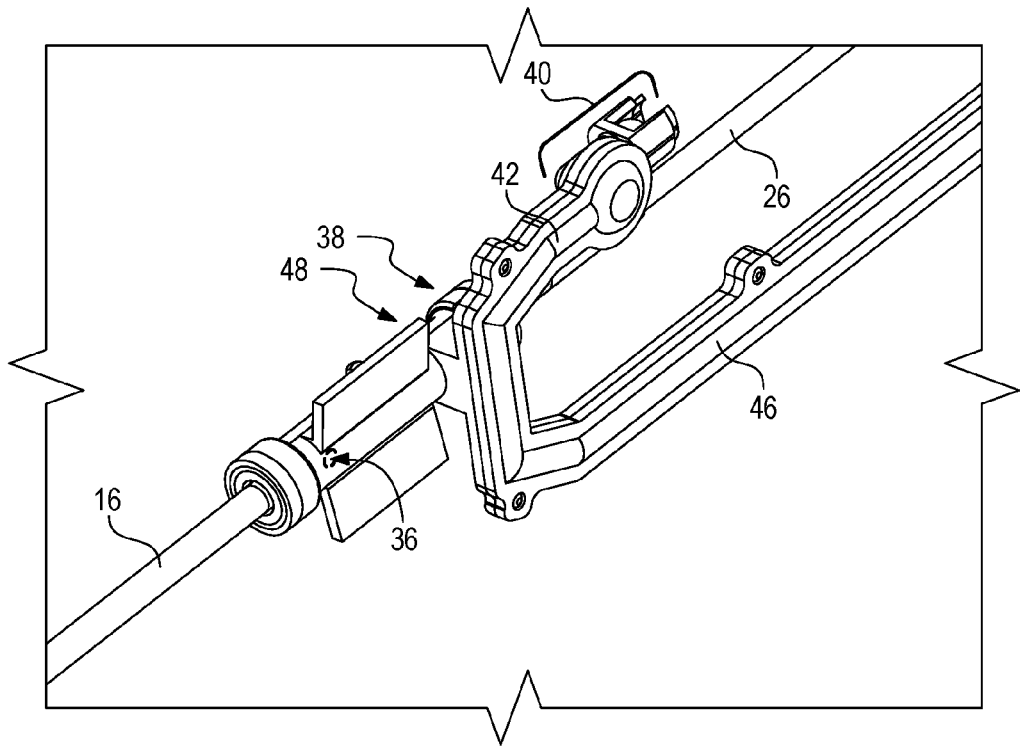
FIGS. 16 and 17 are detailed perspective views of the inner and outer cannulas and the aspiration and irrigation system of the biopsy device depicted in FIG. 1, with portions shown in phantom for clarity.
Figure 17:
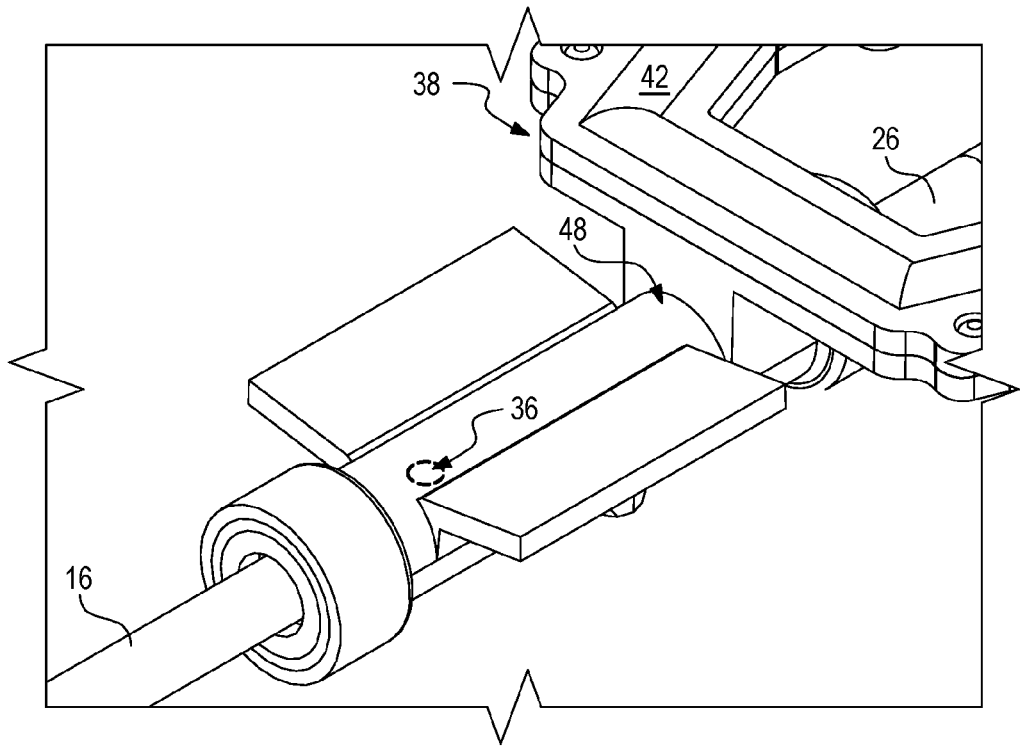
Figure 18:
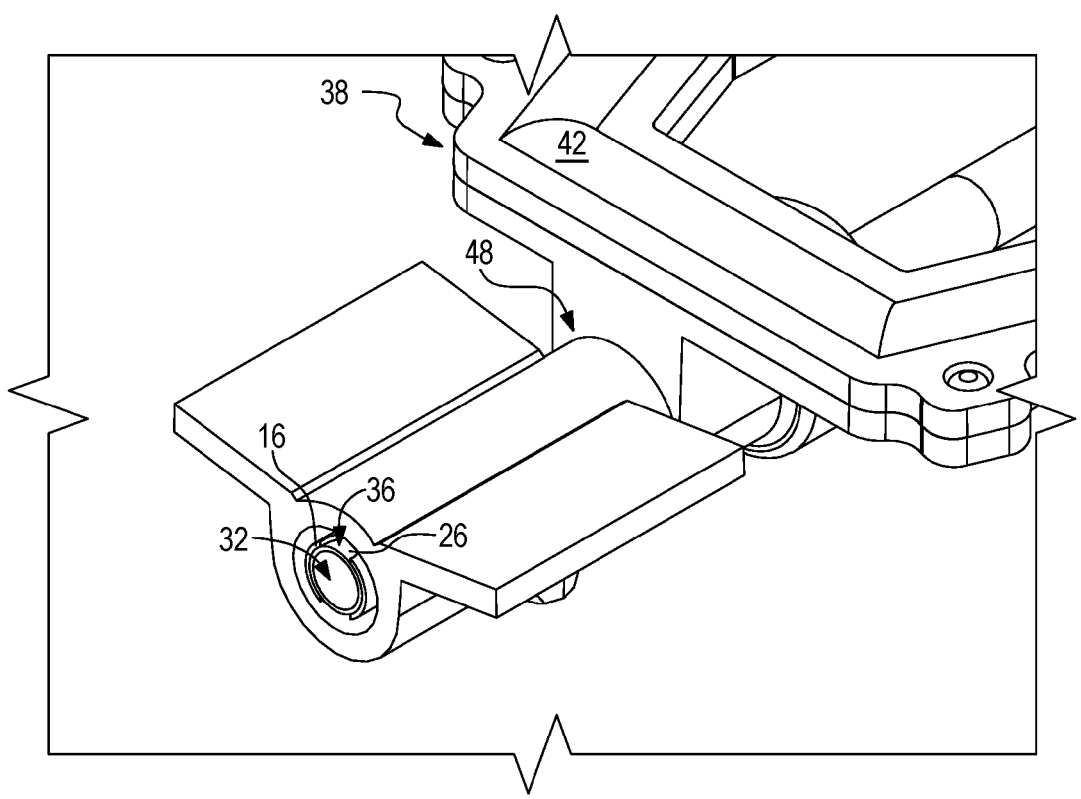
FIG. 18 is an axial cutaway view through the inner and outer cannulas and the aspiration and irrigation system of the biopsy device depicted in FIG. 1, with portions shown in phantom for clarity. The axial cutaway is at the level of the side openings in the outer cannula.

FIGS. 16 and 17 depict the side opening 36 in the outer cannula 16 with the manifold 48 shown in phantom illustrate the fluid coupling of the manifold 48 with the side opening 36. FIG. 18 is an axial cutaway view through the manifold 48 and the outer and inner cannulas 16, 26 at the axial position of the side opening 36. FIG. 18 illustrates the fluid coupling of the manifold 48 with the annular lumen 34 via the side openings 36.

Figure 19:
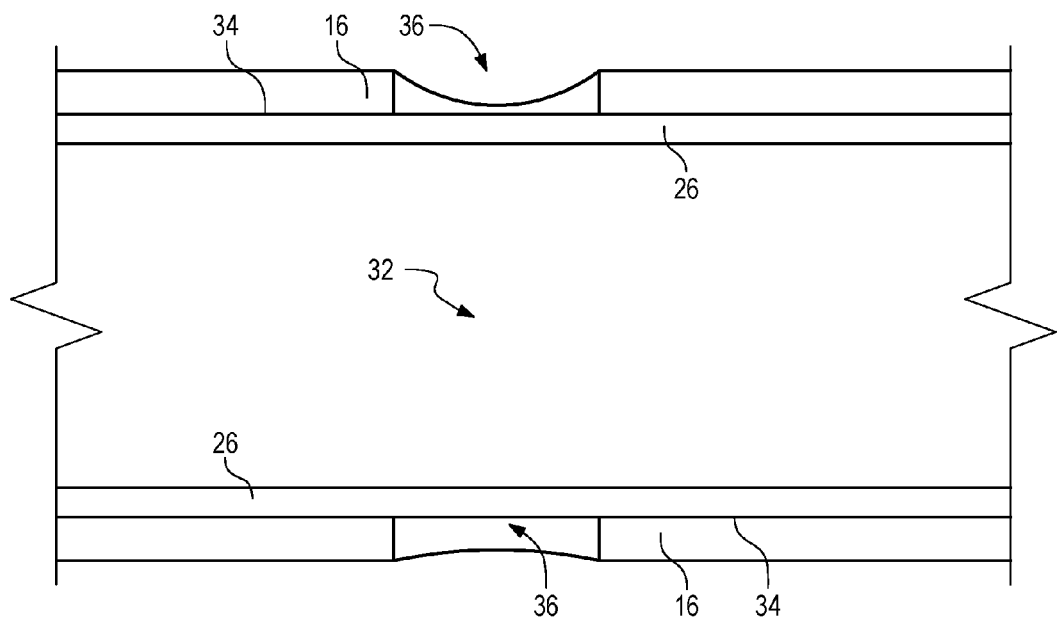
FIGS. 19 and 20 are detailed in greater detail longitudinal cutaway views through the inner and outer cannulas of the biopsy device depicted in FIG. 1 at the level of the side openings in the outer cannula.
Figure 20:
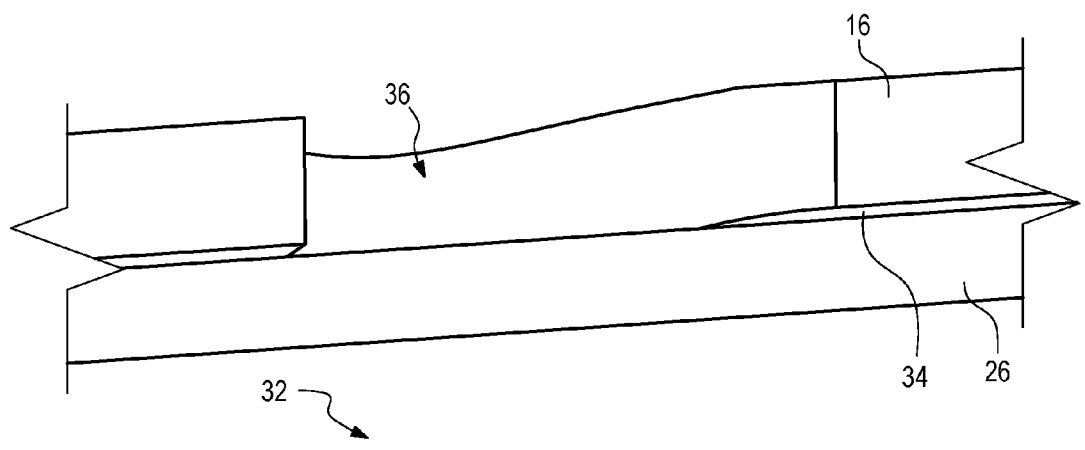

FIGS. 19 and 20 detailed longitudinal cross-sectional views through the outer and inner cannulas 16, 26 at the axial position of the side opening 36. The views in FIGS. 19 and 20 are not perpendicular to the longitudinal axis of the outer and inner cannulas 16, 26 in order to illustrate curvature of side opening 36. All other components of the disposable needle portion 14 of the biopsy device 10 are omitted for clarity. FIGS. 19 and 20 depict the annular lumen 34 between the outer and inner cannulas 16, 26. They also depict the communication of the annular lumen 34 with the side openings 36 in the outer cannula 16.

Figure 21:
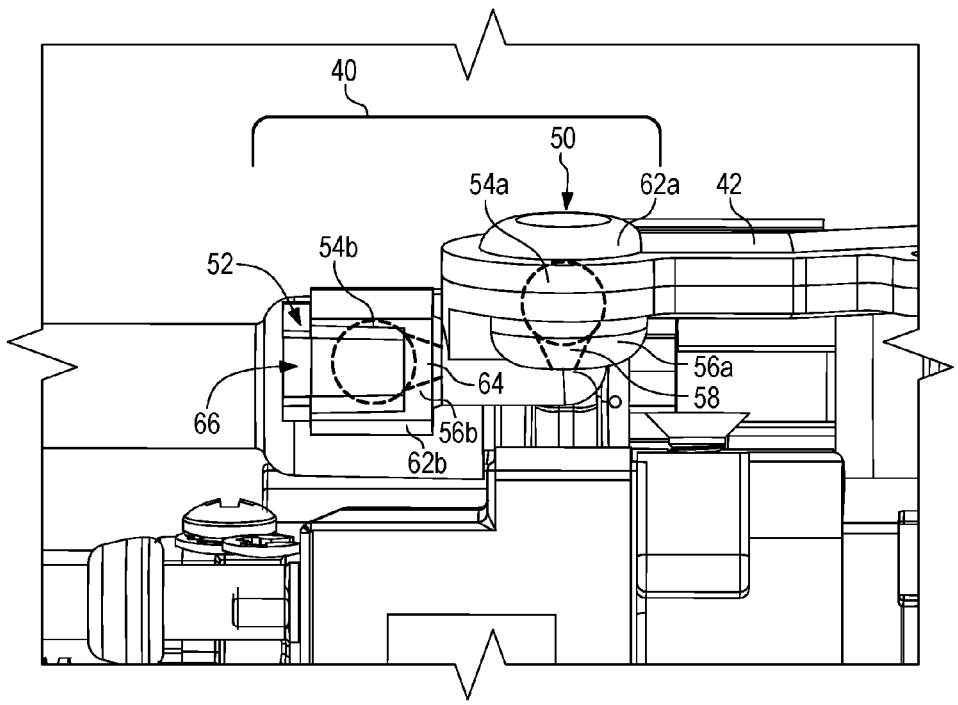
FIG. 21 is a side view of the aspiration vent of the aspiration and irrigation system of the biopsy device depicted in FIG. 1, with portions shown in phantom for clarity.

FIG. 21 depicts an aspiration vent 40 according to one embodiment, with portions thereof shown in phantom to facilitate depiction of internal components. In FIG. 21, the distal end of the biopsy device is pointed to the right of the figure. The aspiration vent 40 includes check and aspirate valves 50, 52, which are configured to close the aspiration vent 40 during vacuum-mediated and pressure-mediated irrigation, respectively (described below).

The check valve 50 includes an interference member 54a disposed in a chamber 62a adjacent an upwardly-facing opening 58 of an interference member seat 56a. The upwardly-facing opening 58 fluidly connects the aspiration line 42 to the atmosphere through the aspirate valve 52. The depicted interference member 54a is spherical, and the depicted upwardly-facing opening 58 is circular. However, in other embodiments, the interference member 54a and upwardly-facing opening 58 can have any respective complementary shapes. When the biopsy device 10 is mounted in position for biopsy, the interference member 54a sits in the interference member seat 56a and partially seals the upwardly-facing opening 58. The interference member 54a is forced distally into the interference member seat 56a when liquid is delivered under pressure through the irrigation input 44 and irrigation line 46 because the check valve is fluidly connected to the irrigation line 46 through the manifold 48. Accordingly, when liquid is delivered under pressure through the irrigation input 44 and irrigation line 46, the seal in the check valve 50 is strengthened and becomes substantially fluid-tight. The seal in the check valve 50 facilitates delivery of liquid from the irrigation input 44 and irrigation line 46, through the manifold 48, side openings 36 and annular lumen 34, and out the tissue receiving opening 20 when the inner cannula lumen 32 is sealed by the cutting board 22 (described below). Examples of liquids that may be delivered under pressure include anesthetics, which may be injected into the irrigation input 44 by a syringe (not shown).

Like the check valve 50, the aspirate valve 52 includes an interference member 54b disposed in a chamber 62b adjacent an interference member seat 56b. However, the interference member seat 56b in the aspirate valve 52 has a side-facing opening 64 instead of an upwardly-facing one. The side-facing opening 64 connects the aspiration line 42 to the atmosphere through the check valve 50 and the aspirate valve 52. The chamber 62b of the aspirate valve 52 also includes a longitudinal opening 76 to facilitate actuation of the aspirate valve 52 (described below). The depicted interference member 54b is spherical, and the depicted side-facing opening 64 is circular. However, in other embodiments, the interference member 54b and side-facing opening 64 can have any respective complementary shapes. The chamber 62b also includes a side-facing atmospheric opening 66 that opens into the interior of the disposable needle portion 14 of the biopsy device 10, which is in turn open to the atmosphere through small openings (not shown) in the housing of the disposable needle portion 14 of the biopsy device 10. Accordingly, the aspiration and irrigation system 38 and the disposable needle portion 14 of the biopsy device 10 selectively communicate with the atmosphere through the atmospheric opening 66 in the aspirate valve 52.

When the biopsy device 10 is mounted in position for biopsy, and before vacuum is applied, gravity causes the interference member 54b to sit on the bottom of the chamber 62b of the aspirate valve 52, and does not seal the interference member seat 56b therein. During vacuum-assisted biopsies, a vacuum source (not shown) is connected to the proximal end of the inner cannula 26 while the distal end 28 of the inner cannula 26 is retracted proximally from the cutting board 22, thereby facilitating fluid communication between the vacuum source and the inner cannula lumen 32. When the vacuum source is connected to the aspiration and irrigation system 38, the vacuum pulls the interference member 54b in the aspirate valve 52 into the side-facing opening 64 with sufficient force to substantially close the side-facing opening 64 in the aspirate valve 52. Further, the vacuum also pulls the interference member 54a in the check valve 50 away from the upwardly-facing opening 58, thereby unblocking the upwardly-facing opening 58. Alternatively, chamber 62b may be configured to (e.g., have elastic walls that are biased to) cause interference member 54b to seal the side-facing opening 64, even in the absence of vacuum, unless the seal is broken by peg 74. In such embodiments, the chamber 62b may not include a seating member.

When the vacuum source is connected to the aspiration and irrigation system 38, the vacuum also pulls liquid from an irrigation source (not shown) connected to the irrigation input 44. Examples of such liquids include saline. With the aspirate valve 52 closed by the interference member 54b, the liquid from the irrigation source travels through irrigation input 44, the irrigation line 46, the manifold 48, the side openings 36 and the annular lumen 34 to enter the inner cannula lumen 32, thereby facilitating transport of excise tissue through the inner cannula 26 (described below). The use of fluids to facilitate tissue transport during a biopsy procedure is described in U.S. patent application Ser. No. 13/383,318, U.S. National entry filed on Jan. 10, 2012 of PCT/US2011/062148 with international filing date Nov. 24, 2011, and assigned to the same assignee as the instant application, the contents of which are incorporated by reference as though fully set forth herein. In other embodiments, a saline valve (e.g., a pinch valve; not shown) may be provided to additionally control the flow of liquid through the system 38. For instance, the saline valve may be disposed in the biopsy console downstream of the saline source.

Figure 22:
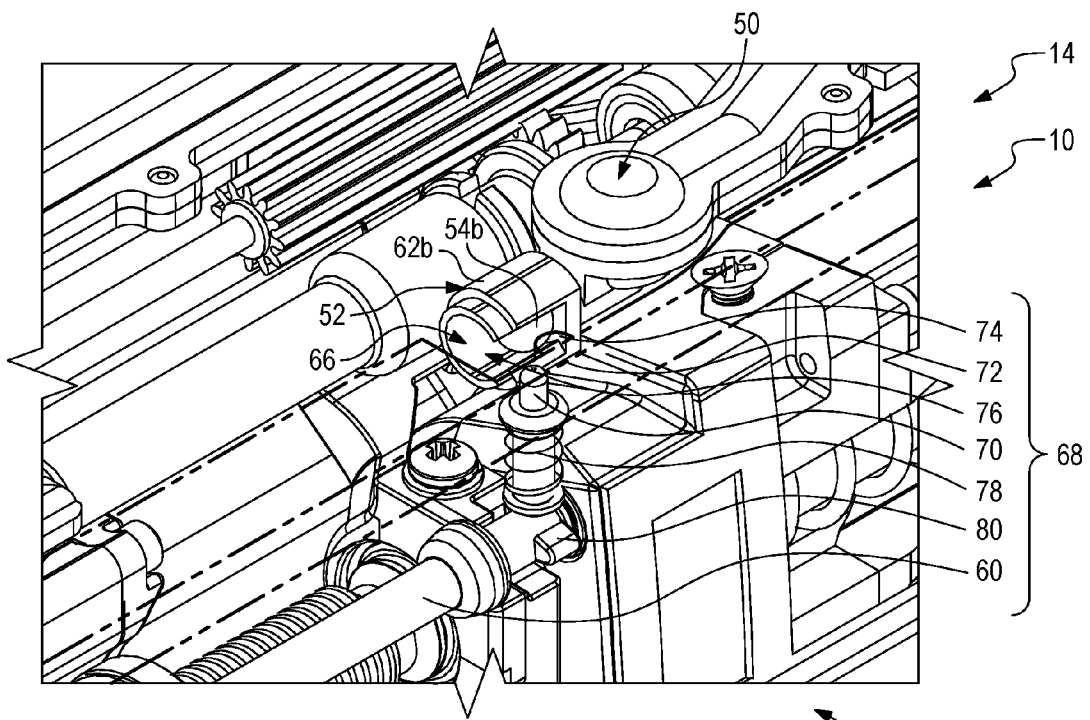
FIGS. 22 and 24 are perspective views of the biopsy device depicted in FIG. 1, with select components omitted to allow visualization of the aspiration vent of the aspiration and irrigation system and the peg of the actuation mechanism.

FIG. 22 depicts an actuation mechanism 68 configured to selectively open the aspirate valve 52 of the aspiration vent 40 when a vacuum source is connected to the aspiration and irrigation system 38. The actuation mechanism 68 includes an elongated cam 60, a vertical cam follower 70, a deflection surface 72, and a horizontal peg 74. The cam 60 has a distal end 80 in contact with the vertical cam follower 70, which is in contact with the deflection surface 72. The deflection surface 72 is coupled to the horizontal peg 74. In other embodiments, the deflection surface 72 may be in contact with, rather than coupled to, the horizontal peg 74. The deflection surface 72 is approximately diagonal to both the vertical cam follower 70 and the horizontal peg 74. Accordingly, vertical motion by the cam follower 70 is transformed to horizontal motion of the peg 74. The deflection surface 72 is an extension of the frame of the disposable needle portion 14 of the biopsy device 10 and it is formed from an elastic material. As such, the deflection surface 72 and peg 74 attached thereto are biased away from a longitudinal opening 76 and the interference member 54b of the aspirate valve 52. The cam follower 70 is disposed in a lumen of a spring 78, which biases the cam follower toward the cam distal end 80 and away from the deflection surface 72.

The cam 60 and a method of controlling movement of various components of the biopsy device 10, including the interference member 54b of the aspirate valve 52, by rotating the cam 60 are described in detail in U.S. Provisional Patent Application Ser. No. 62/055,610, which has been previously incorporated by reference. By also using the cam 60 to actuate the aspirate valve 52, the number of parts and the size of the reusable body portion 12 is minimized. To actuate the aspirate valve 52, the peg 74 of the actuation mechanism 68 enters the chamber 62b of the aspirate valve 52 through the longitudinal opening 76 to dislodge the interference member 54b from the interference member seat 56b.

The actuation mechanism 68 includes components of both the reusable body portion 12 and disposable needle portion 14 of the biopsy device 10. The elongated cam 60 and the vertical cam follower 70 are parts of the reusable body portion 12 of the biopsy device 10. The deflection surface 72 and the horizontal peg 74 are parts of the disposable needle portion 14 of the biopsy device 10. The vertical cam follower 70 extends vertically out of the reusable body portion 12, and enters a bottom surface of the disposable needle portion 14 to interact with the horizontal peg 74 via the deflection surface 72. This arrangement minimizes the possibility of contamination of the patient because air entering the aspiration and irrigation system 38 through atmospheric opening 66, when aspirate valve 52 is open, passes over sterile components in the disposable needle portion 14 rather than the clean components in the reusable body portion 12. Because the clean vertical cam follower 70 only contacts the deflection surface 72, which is separated from the sterile interference member 54 of the aspirate valve 52 by the sterile horizontal peg 74, the possibility of contamination of the patient is substantially minimized.

Figure 23:
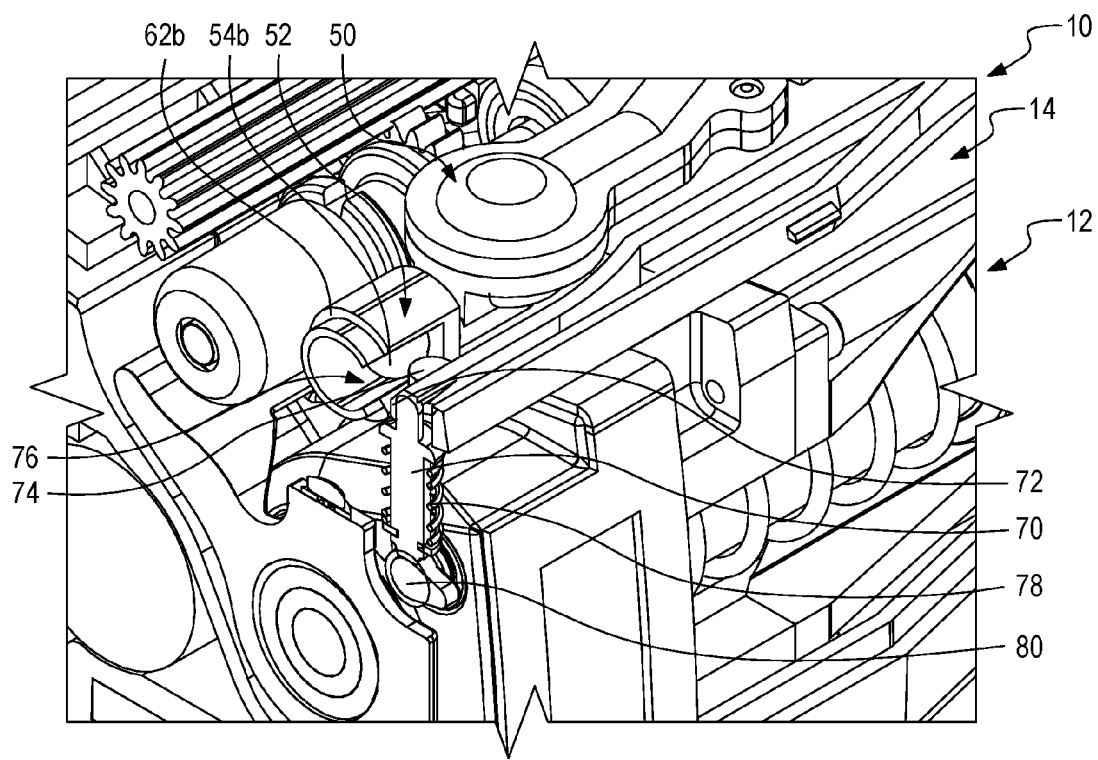
FIG. 23 is an axial cutaway view through the biopsy device depicted in FIG. 1, with select components omitted to allow visualization of the aspiration vent of the aspiration and irrigation system and the peg of the actuation mechanism.

FIG. 23 is a cutaway view through the reusable body portion 12 and disposable needle portion 14 of the biopsy device 10 from an approximately axial direction, with certain components omitted and the vertical cam follower 70 shown in phantom for clarity. The distal end 80 of the elongate cam 60, which is configured to interact with the cam follower 70, is shaped like an eccentric wheel, thereby facilitating the cam distal end's 80 function of transforming rotary motion into linear motion. The cam distal end 80, like all eccentric wheels, has a surface diameter between a largest diameter and a smallest diameter.

Figure 24:
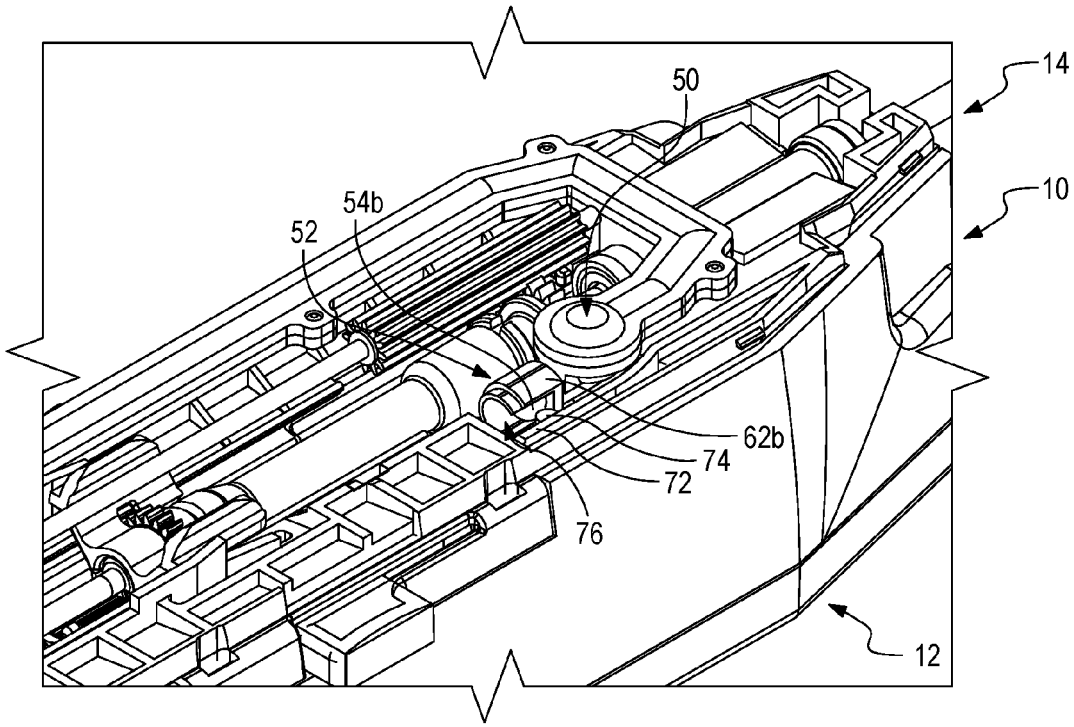
Figure 25:
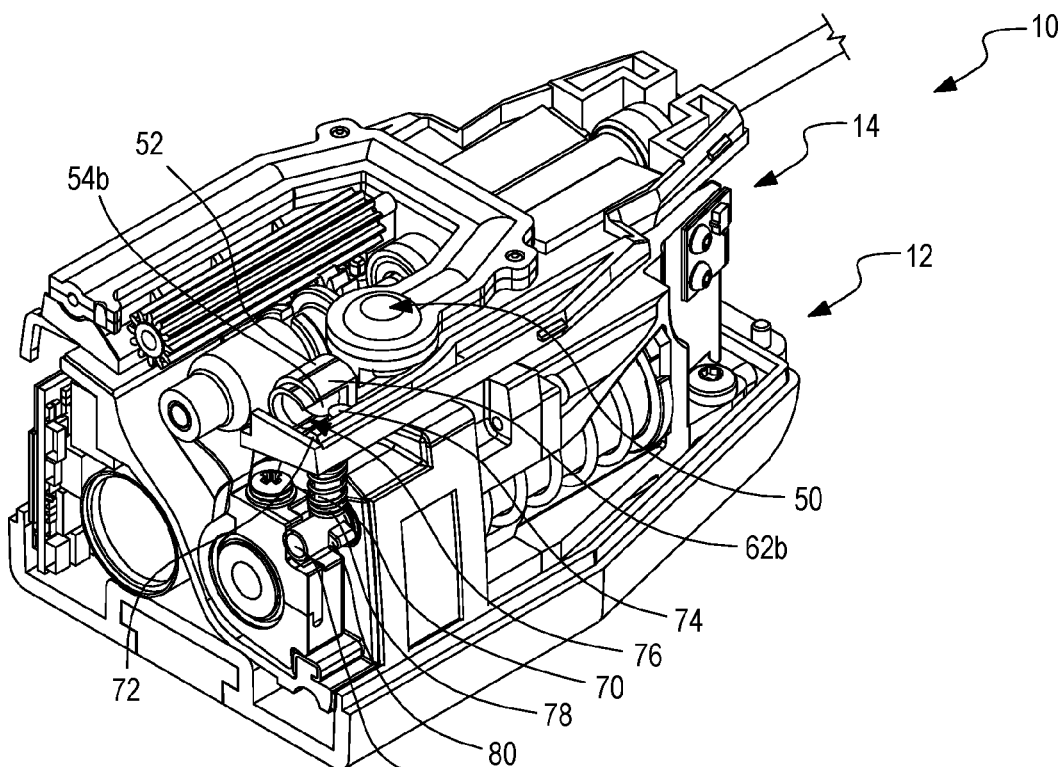
FIGS. 25 to 28 are a series of axial cutaway view through the biopsy device depicted in FIG. 1, with select components omitted to allow visualization of the aspiration and irrigation system and the actuation mechanism.
Figure 26:
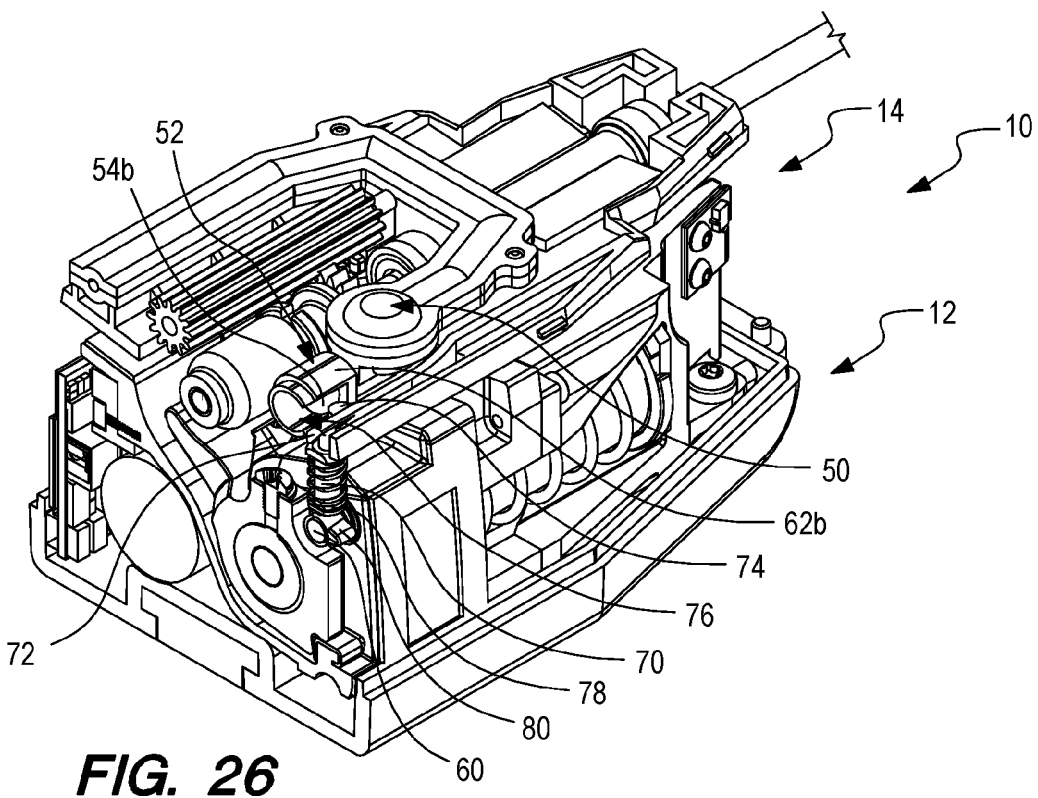
Figure 27:
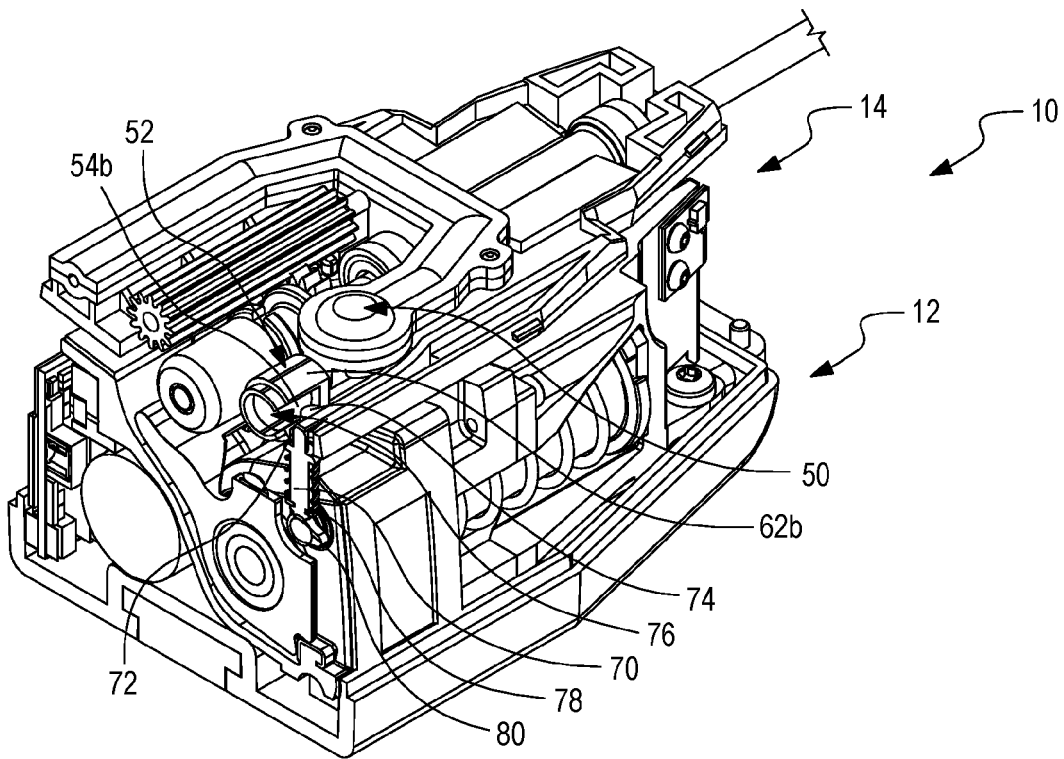
Figure 28:
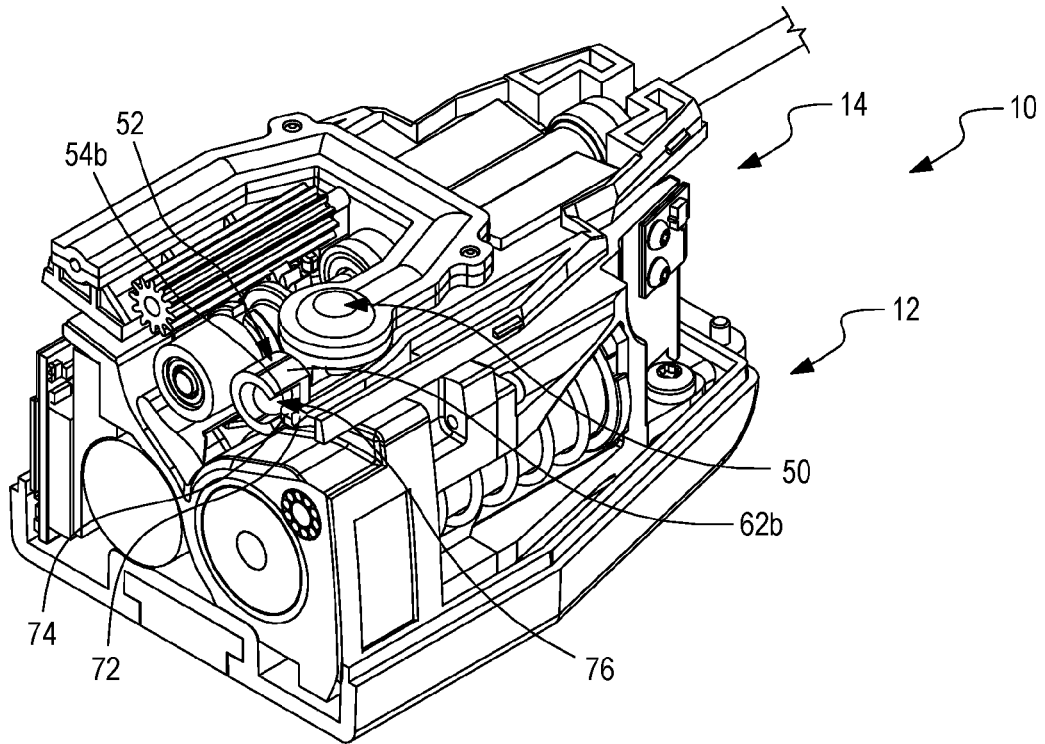

FIG. 24 is a perspective view of the biopsy device 10 with certain components omitted to show the juxtaposition of the interference member 54*b* of the aspirate valve 52 and the horizontal peg 74. FIGS. 25 to 28 are cutaway views of the biopsy device 10, through axial planes that move distally along the longitudinal axis of the biopsy device 10, with certain components omitted to show the interaction between the components of the actuation mechanism 68 and the aspirate valve 52. FIG. 27 illustrates the interaction between the cam 60, the cam follower 70 and the deflection surface 72. FIG. 28 illustrates the interaction between the peg 74 and the interference member 54*b* in the aspirate valve 52. In FIGS. 22 to 28, the cam 60 is rotated such that the smallest diameter surface of the cam distal end 80 is in contact with the cam follower 70. As such, the cam follower 70 is biased in its lowest position by the spring 78 and the horizontal peg 74 is biased away from the interference member 54*b* in the aspirate valve 52.

When the cam 60 is rotated such that the largest diameter surface of the cam distal end 80 is in contact with cam follower 70. Rotating the cam 60 (and the cam distal end 80) into this position overcomes the expansive force of the spring 78, and pushes the cam follower 70 up into the deflection surface 72. The deflection surface 72 translates the vertical motion of the cam follower 70 into horizontal motion of the horizontal peg 74. Horizontal motion of the peg 74 brings it into contact with the interference member 54*b* in the aspirate valve 52. Continued horizontal motion of the peg 74 dislodges the interference member 54*b* from the side-facing opening 64 in the interference member seat 56*b* in the aspirate valve 52, thereby allowing the site-facing opening 64 to communicate with the atmosphere through the atmospheric opening 66 in the aspirate valve 52. Because the aspirate valve 52 is connected to the inner cannula lumen 32 via the aspiration and irrigation system 38, when the cam 60 is rotated to dislodged the interference member 54*b* in the aspirate valve 52, a vacuum generated in the inner cannula lumen 32 (e.g., by a vacuum source) is released/vented by communication with the atmosphere through the aspiration vent 40.

Having described the structure of various components of the biopsy device 10, including the aspiration interrogation system 38 and the actuation mechanism 68, a biopsy procedure 100 using the biopsy device 10 will now be described. FIG. 31 summarizes the steps of a vacuum-assisted biopsy procedure 100 according to one embodiment. The summary in FIG. 31 also includes the states of the check and aspirate valves 50, 52 and various irrigation and aspiration/venting related functions at the respective steps. The steps summarized in FIG. 31 can be in addition to the biopsy procedure 100 that is described in detail in U.S. Provisional Patent Application Ser. No. 62/055,610, which has been previously incorporated by reference.

At step 102, a user (e.g., a physician and/or a technician working under the direction of a physician) mounts the biopsy device 10 to a stable surface like a stereotactic surgical table. When the biopsy device 10 is first mounted, the inner cannula 26 is in its distal most location, with its distal end 28 against the cutting board 22 in the outer cannula lumen 24. Further, the vacuum is off and no liquid is introduced into the aspiration and irrigation system 38 under pressure. As such, the check and aspirate valves 50, 52 are open and venting is possible. However, because the vacuum is off, there is no vacuum to vent.

Before step 104, distal portions of the outer and inner cannulas 16, 26 have already been inserted into the tissue to be biopsied. At step 104, a liquid (e.g., saline and/or anesthesia) is delivered to the tissue adjacent the tissue receiving opening 20 in the outer cannula 16. The delivered liquid can also travel in a retrograde fashion along the path of the outer cannula 16 ultimately into the tissue, where anesthetic can relieve pain associated with the procedure. At step 104, the vacuum remains in an off position, therefore the aspirate valve 52 remains open. At step 104, the inner cannula 26 is still in its distal most location against the cutting board 22. Accordingly, when the liquid is delivered through the irrigation input 44 and the irrigation line 46 under pressure (by using a syringe), the liquid cannot enter the inner cannula lumen 32. Further, the liquid cannot exit the aspiration and irrigation system 38 through the aspiration vent 40 because the check valve 50 is closed by the liquid under pressure. Therefore, the liquid exits the outer cannula lumen 24 via the only open exit, i.e., the tissue receiving opening 20, and flows into the tissue as described above.

At step 106, the inner cannula 26 remains in its distal most location against the cutting board 22. However, the introduction of pressurized liquid into the aspiration and irrigation system 38 via the irrigation input 44 at step 104 is terminated. As a result, the check valve 50 opens, and remains open from step 106 to step 116. Further, the vacuum source is turned on and delivers vacuum to the inner cannula 26, and remains on from step 106 to step 116. However, because the distal end 28 of the inner cannula 26 is blocked by the cutting board 22 in step 106, the vacuum source is not in fluid communication with the aspiration and irrigation system 38 via the outer cannula 16. As a result, although the aspirate valve 52 remains open, venting does not occur to any substantial degree. Moreover, with a lack of pressure and vacuum in the aspiration and irrigation system 38, liquid flow through the system 38 is minimal to none.

At step 108, the inner cannula 26 begins moving proximally away from the cutting board 22 to prepare for the first cutting stroke, thereby exposing its open distal end 28, and fluidly connecting the inner cannula lumen 32 to the annular lumen 34. Because the vacuum source remains on and connected to the inner cannula 26, the vacuum closes the aspirate valve 52 as described above. Because the aspirate valve 52 is closed, the vacuum is not vented. Because there is no pressurized fluid entering the irrigation input 44, the check valve 50 remains open. Because the aspirate valve 52 is closed, vacuum from the vacuum source pulls liquid (i.e., saline) through the irrigation input 44 (and not air through the aspirate valve), the irrigation line 46, the manifold 48, side openings 36, the annular lumen 34, and into the inner cannula lumen 32 through the open distal end 28 thereof. Since step 108 precedes the first cutting stroke, there is no excised tissue in the inner cannula lumen 32. Therefore, the liquid entering the aspiration and irrigation system 38 through the irrigation input 44 flows through the inner cannula lumen 32 unobstructed.

At step 110, the inner cannula has reached its proximal most location, and the first cutting stroke and is ready to begin. As in step 108, the vacuum source remains powered on and connected to the inner cannula 26, the aspirate valve 52 remains closed, the check valve 50 remains open, the vacuum is not vented, and thus liquid flows under vacuum. Before the first cutting stroke, there still is no excised tissue in the inner cannula lumen 32. Therefore the liquid continues to flow through the inner cannula lumen 32 unobstructed.

The cutting stroke starts at step 112, when the inner cannula begins to move distally from its proximal most location. As in steps 108 and 110, the vacuum source remains powered on and connected to the inner cannula 26, the aspirate valve 52 remains closed, the check valve 50 remains open, the vacuum is not vented, and thus liquid flows under vacuum from the irrigation input 44 to the inner cannula lumen 32. Step 112 is the cutting portion of the cutting cycle, during which the inner cannula 26 moves distally from its proximal most location to its distal most location. Excised tissue that is no longer connected to the rest of the tissue will be drawn proximally through the inner cannula lumen 32 by the vacuum source. The liquid flowing from the aspiration and irrigation system 38 facilitates transport of excised tissue. During step 112, the inner cannula 26 rotates as it translates distally to facilitate cutting of tissue.

At step 114, the biopsy device 10 has reached the approximate middle of the cutting cycle, when the inner cannula 26 reaches its distal most location against the cutting board 22. At that point, the inner cannula 26 terminates its axial movement, but continues to rotate to facilitate cutting of tissue. As in steps 108 to 112, the vacuum source remains powered on and connected to the inner cannula 26 and the check valve 50 remains open. However, because the distal end 28 of the inner cannula 26 is closed by the cutting board 22, the aspirate valve 52 is open. Further, the vacuum in the inner cannula lumen 32 is not vented because it is sealed off from the aspiration vent 40 by the cutting board 22. Moreover, because the vacuum does not reach the aspiration and irrigation system 38, liquid flow through the system 38 is minimal to none. Step 114 is similar to step 106 described above.

At step 116, the inner cannula is on the second half, i.e., the retracting portion, of the cutting cycle, during which the inner cannula 26 moves proximally from its distal most position to its proximal most position. During step 116, the excised tissue is separated from the rest of the target site and is moved proximally through the inner cannula lumen 32 under vacuum. As in steps 108 to 114, the vacuum source remains powered on and connected to the inner cannula 26 and the check valve 50 remains open. However, at step 116, the elongate cam 60 is rotated such that the vertical cam followers 70 rises, causing the horizontal peg 74 to move into the chamber 62b of the aspirate valve 52 to thereby dislodge the interference member 54b from the interference member seat 56b. Dislodging the interference member 54b opens the aspirate valve 52 and allows vacuum distal of the excised tissue in the inner cannula lumen 32 to vent to atmosphere through the aspiration and irrigation system 38. In step 114, liquid flow through the aspiration and irrigation system 38 is minimal to none because the vacuum is being vented through the system 38. In one embodiment, a controller in the biopsy device 10 activates a motor that rotates the elongate cam 60 to open the aspirate valve 52. The inner cannula 26 continues to rotate during step 116.

Venting the vacuum distal of the excised tissue increases the pressure imbalance proximal and distal of the excised tissue, thereby increasing the rate at which the excised tissue travels through the inner cannula lumen 32. Increasing the pressure imbalance also prevents excised tissue from becoming trapped in the inner cannula lumen 32 due to increasing vacuum distal of the excised tissue that cannot be vented.

After step 116, steps 114 to 116 can be repeated until the biopsy is completed. While the biopsy procedure 100 described above includes "turning on and connecting" a vacuum source, the vacuum source may be permanently turned on and selectively connected to and disconnected from the inner cannula lumen 32 at the appropriate steps in the procedure.

In an alternative embodiment, the aspiration vent 40 is located in the reusable body portion 12 of the biopsy device 10. In such embodiments, a filter in the disposable needle portion 14 would prevent liquids from entering the aspiration vent 40 in the reusable body portion 12. Therefore, the filter prevents contamination of the reusable body portion 12. After each biopsy, the filter would be disposed of along with the disposable needle portion 14. In one embodiment, the filter is 0.22 μm or smaller to prevent contamination of the reusable body portion 12.

In another alternative embodiment, the aspirate valve 52 can be actuated via the dwell spring, which is described in detail in U.S. Provisional Patent Application Ser. No. 62/055,610, which has been previously incorporated by reference. A lever or cam can be driven by retraction of the dwell spring mechanism to actuate open the aspirate valve 52. Actuating the aspirate valve 52 via the dwell spring would mechanically link the venting of vacuum distal of excised tissue in the inner cannula lumen 32 with retraction of the inner cannula 26 after each cutting stroke. In yet another alternative embodiment, the aspirate valve 52 can be actuated via a solenoid that is controlled by the biopsy device controller.

In still another alternative embodiment, the cylinder surrounding the side opening 36 in the outer cannula 16 and fluidly coupled to the manifold 48 can be increased in size to increase the rate of liquid flow through the aspiration and irrigation system 38.

Figure 32:
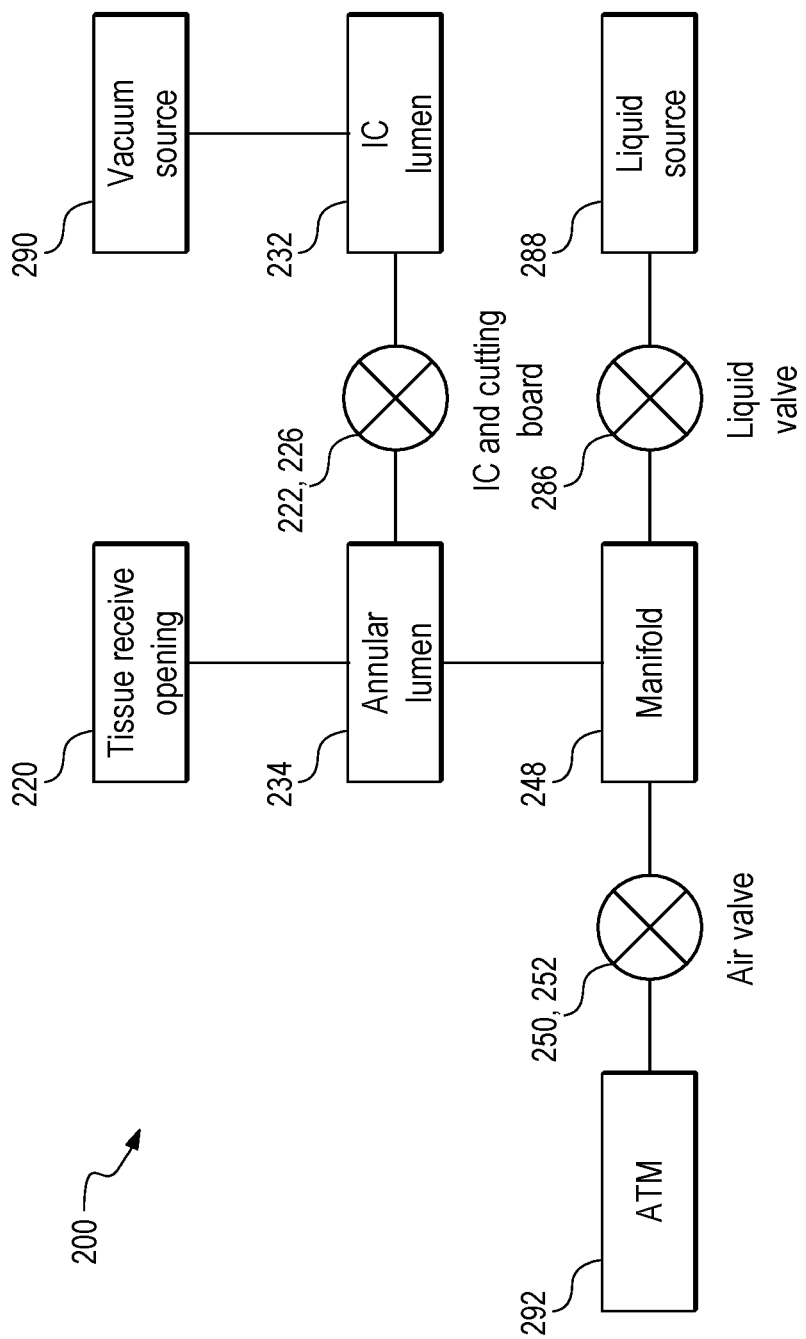
FIG. 32 is a system diagram schematically depicting a biopsy device according to one embodiment.

FIG. 32 is a system diagram schematically depicting a vacuum-assisted biopsy device 200 according to another embodiment. The biopsy device 200 depicted in FIG. 32 is almost identical to the biopsy device 10 described above, except that the biopsy device 200 depicted in FIG. 32 includes a liquid valve 286 (e.g., a pinch valve) disposed between a liquid source 288 and a manifold 248. The liquid valve 286 can also be called a saline valve 286. As in the biopsy device 10 described above, the manifold 248 in FIG. 32 is also fluidly coupled to an annular lumen 234 and an air valve 250, 252, which is for aspiration to atmosphere 292. The air valve 250, 252 includes a check valve 250 and an aspirate valve 252, which are similar to respective check valve 50 and aspirate valve 52 described above with respect to biopsy device 10.

While this embodiment includes a liquid valve/saline valve 286, biopsy devices according to other embodiments do not include a liquid valve/saline valve. In such embodiments, liquid/saline flow may be controlled by positive pressure and vacuum in the system.

FIG. 32 depicts air and liquid flow in the biopsy device 200. The vacuum source 290 is fluidly coupled to a proximal end of the inner cannula lumen 232, which is in turn, selectively fluidly coupled to the annular lumen 234 (defined between inner and outer cannulas, not shown). The annular lumen 234 is fluidly coupled at the proximal end to the tissue receiving opening 220, which leads outside of the distal end of the outer cannula (not shown) and at the distal end to the manifold 248. The manifold 248 is selectively fluidly coupled to the liquid source 288 (via liquid valve 286) and atmosphere 292 (air valve 250, 252). While there is no "valve" between the inner cannula lumen 232 and the annular lumen 234, these two lumens 232, 234 are only fluidly coupled to each other when the inner cannula 226 is retracted proximally away from the cutting board 222.

Figure 33:
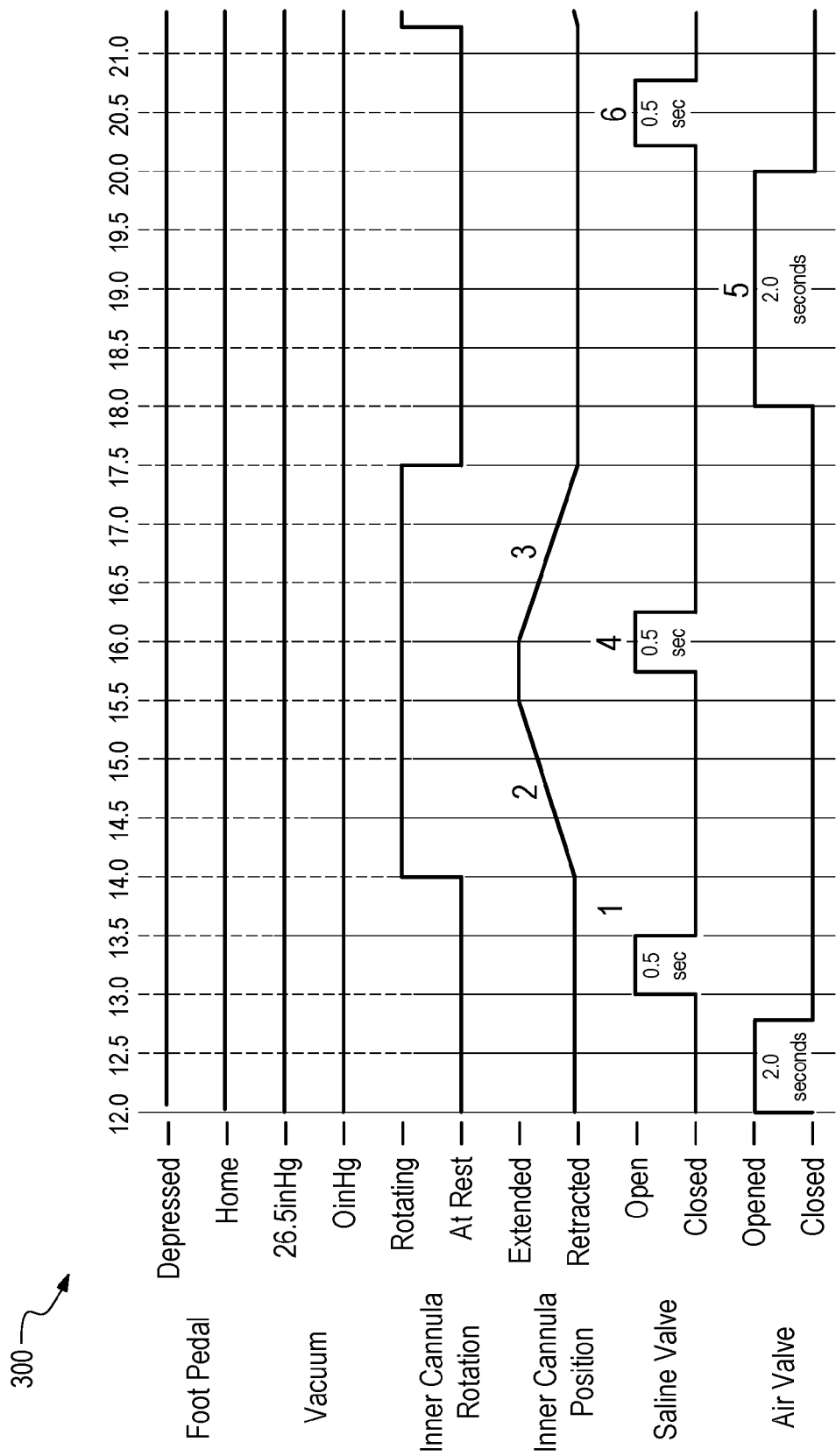
FIG. 33 is a timing diagram illustrating the steps of a vacuum-assisted biopsy procedure according to one embodiment.

FIG. 33 is a timing diagram illustrating the steps of a vacuum-assisted biopsy procedure 300, according to another embodiment, using the biopsy device 200 depicted in FIG. 32. FIG. 34 is a table 400 summarizing the steps of the vacuum-assisted biopsy procedure 300 illustrated in FIG. 33. Steps 1 to 6 represent one cutting cycle using the biopsy device 200.

Step 1, i.e., "pre-cut vacuum," follows completion of the previous cutting cycle, which concludes with a post-aspirate lavage. Thus Step 1 begins with closing of the liquid valve 286 (e.g., at 13.5 s in FIG. 33). In FIGS. 33 and 34, the liquid valve 286 is labeled "saline valve." During Step 1, which lasts about 0.5 s, vacuum builds in the biopsy device 200 thereby drawing tissue into tissue receiving opening 220. Step 1 concludes when the inner cannula is fully proximally retracted, the liquid valve 286 is closed, and the air valve 250, 252 is closed.

Step 2, i.e., "biopsy cut," begins after completion of Step 1 ("pre-cut vacuum"). Optionally, Step 2 begins after receipt of a Core Index Complete Message, in systems with indexing core collection chambers, such as those described in U.S. patent application Ser. No. 13/383,318, the contents of which are incorporated by reference as though fully set forth herein. During Step 2, which lasts less than 2 s (about 1.75 s in FIG. 33), the inner cannula 226 moves from the fully proximally retracted position to the fully distally extended position while rotating to cut tissue prolapsing through the tissue receiving opening 220. Step 2 concludes just before the inner cannula 226 reverses rotation, the liquid valve 286 is closed and the air valve 250, 252 is closed.

Step 3, i.e., "IC retraction," begins when the inner cannula 226 reverses rotation at the end of Step 2. During Step 3, which lasts less than 2 s (about 1.75 s in FIG. 33), the inner cannula 226 unwinds the dwell spring for about the first 0.25 s, and then retracts from the fully distally extended position to the fully proximally retracted position while rotating in the reverse direction. The liquid valve 286 is open during the first 0.5 s of Step 3 (see Step 4 below) and the air valve 250, 252 is closed.

There is a dwell period that overlaps Steps 2 and 3, as described in detail in U.S. Provisional Patent Application Ser. No. 62/055,610, which has been previously incorporated by reference. During the dwell period, which lasts about 0.5 s, the inner cannula 226 is positioned at its fully distally extended position against the cutting board 222, and continues to rotate (in the same direction as during the rest of Step 2) to completely sever the prolapsing tissue.

Step 4, i.e., "Pre-Aspirate Lavage," which overlaps the first 0.5 s of Step 3, is triggered by reversal of the motor that rotates the inner cannula 226 at the end of Step 2. During Step 4, which lasts about 0.5 s, the inner cannula 226 rotates and unwinds the dwell spring for about the first 0.25 s, and then begins to retract from the fully distally extended position in a proximal direction. The liquid valve 286 is open and the air valve 250, 252 is closed. Opening the liquid valve 286 during Step 4 allows a bolus of liquid (e.g., saline) to be introduced into the device 200. Because the air valve 250, 252 is closed, the bolus of liquid will travel through the manifold 248 and the annular lumen 234, and fill in behind the severed tissue in the inner cannula lumen 232. This liquid facilitates the vacuum assisted proximal travel of the tissue through the inner cannula lumen 232.

Step 5, i.e., "Aspiration," is triggered by completion of Step 3 in that Step 5 is programmed to begin about 2.0 s after completion of Step 3. During Step 5, which lasts at least 2 s (about 2 s in FIG. 33), the inner cannula 226 is at its fully proximally retracted position. The liquid valve 286 is closed and the air valve 250, 252 is open. The air valve may be opened by opening the aspirate valve 252 using an actuation mechanism as described above for the biopsy device 10 depicted in FIGS. 21-28. Opening the air valve releases the vacuum distal of the severed tissue in the inner cannula lumen 232, thereby facilitating the vacuum assisted proximal travel of the tissue through the inner cannula lumen 232.

Step 6, i.e., "Post-Aspirate Lavage," is triggered by completion of Step 5 in that Step 6 is programmed to begin about 0.25 s after completion of Step 5. During Step 6, which lasts about 0.5 s, the inner cannula 226 is at its fully proximally retracted position. The liquid valve 286 is open and the air valve 250, 252 is closed. Opening the liquid valve 286 during Step 6 allows another bolus of liquid (e.g., saline) to be introduced into the device. Because the air valve 250, 252 is closed, the bolus of liquid will travel through the manifold 248 and the annular lumen 234, and into the inner cannula lumen 232. This liquid removes from the inner cannula lumen 232 any tissue remnants from the previous biopsy stroke to prepare the device 200 for the next biopsy stroke.

After Step 6, the biopsy device 200 can cycle through Steps 1-6 to sequentially biopsy additional tissue samples. Although Steps 1-6 are described above as having specific "triggers," these descriptions are intended to be illustrative and not limiting. For instance, while aspiration Step 5 is depicted in FIG. 34 as being "triggered" by completion of inner cannula retraction, the aspiration step can be programmed to begin at any time relative to an event in the biopsy procedure 300, including a predetermined amount of time after an event (e.g., 0.5 s after liquid valve closes). Note that in the method 100 depicted in FIG. 31 and previously described, the aspiration step is begins at the same time that the inner cannula 26 begins to move proximally from the distal most position.

While the embodiments described herein have a particular aspiration valve structure, that structure is illustrative and not intended to be limiting. Accordingly, the actuating mechanism described herein can be used to open any suitable valve, including those without seating members.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

The invention claimed is:

1. A biopsy system, comprising:
(a) an instrument set, the instrument set comprising an instrument set housing,
an elongate outer cannula having an axial lumen, a proximal portion coupled to the instrument set housing, and a distal portion having a tissue receiving aperture in a side wall thereof in communication with the lumen, an elongate inner cannula disposed within the outer cannula lumen, an aspiration vent disposed within the instrument set housing, wherein the aspiration vent fluidly couples the outer cannula lumen to atmosphere through an aspiration vent opening, an aspirate valve assembly interposed in the aspiration vent, the aspirate valve assembly including a sealing member configured to seal the aspiration vent opening, and an interference member that may be selectively moved at least partially into the aspiration vent opening to thereby contact the sealing member and prevent the sealing member from sealing the aspiration vent opening: and (b) an instrument drive removably coupled to the instrument set, the instrument drive comprising an instrument drive housing removably coupled to the instrument set housing, a motorized inner cannula driver disposed within the instrument drive housing and configured to axially oscillate the inner cannula relative to the outer cannula during operation of the biopsy system, such that an open distal end of the inner cannula moves back and forth across the tissue receiving aperture to sever tissue extending therethrough, and an actuating member disposed within the instrument drive housing, wherein the actuating member is configured to selectively move the interference member at least partially into the vent opening to thereby prevent the sealing member from sealing the aspiration vent opening.

2. The biopsy system of claim 1, the instrument drive comprising a rotatable cam disposed within the instrument drive housing, wherein selective rotation of the cam moves the actuating member into contact with the interference member.

3. The biopsy system of claim 2, the instrument drive further comprising a motorized cam driver disposed within the instrument drive housing, the motorized cam driver having an output operatively coupled to the cam for rotating the cam between a first position, in which the cam does not move the actuating member into actuate the interference member, and a second position, in which the cam moves the actuating member into the interference member.

4. The biopsy system of claim 3, wherein the motorized cam driver is processor controlled to selectively rotate the cam into and out of the first position depending upon a respective position and a direction of travel of the inner cannula relative to the outer cannula.

5. The biopsy system of claim 1, wherein when the aspiration vent opening is not sealed, the outer cannula lumen is vented to a non-sealed interior of the instrument set housing through the aspiration vent opening.

6. The biopsy system of claim 1, wherein the aspirate valve assembly is configured such that the sealing member seals the aspiration vent opening unless the interference member is at least partially within the vent opening to thereby prevent the sealing member from sealing the aspiration vent opening.

7. The biopsy system of claim 6, wherein the aspirate valve assembly is configured such that the sealing member seals the aspiration vent opening when a vacuum is supplied through the outer cannula.

8. The biopsy system of claim 7, wherein the aspirate valve assembly further comprises a valve chamber, and wherein the sealing member is disposed in the valve chamber.

9. The biopsy system of claim 8, wherein the instrument drive housing is configured for mounting to a stereotactic table adapter, the sealing member comprises a ball, and the aspiration vent opening is being located in a lateral sidewall of the valve chamber, such that, when the instrument drive housing is mounted to the adapter, and the instrument set housing is coupled to the instrument drive housing, the ball falls off the aspiration vent opening under gravitational force in the absence of a vacuum source drawing the ball against the aspiration vent opening.

10. The biopsy system of claim 1, wherein the aspirate valve assembly is configured such that the aspiration vent opening is not sealed unless the vacuum is supplied through the outer cannula.

11. The biopsy system of claim 1, wherein the outer cannula is movable relative to the instrument set housing.

* * * * *